US008283002B2

(12) United States Patent
Brown et al.

(10) Patent No.: US 8,283,002 B2
(45) Date of Patent: Oct. 9, 2012

(54) AMINOBENZENE COMPOSITIONS AND RELATED DEVICES AND METHODS

(75) Inventors: Christopher T. Brown, Pittsburgh, PA (US); Venkataramanan Shesadri, Monroeville, PA (US); Jing Wang, Gibsonia, PA (US)

(73) Assignee: Plextronics, Inc., Pittsburgh, PA (US)

( * ) Notice: Subject to any disclaimer, the term of this patent is extended or adjusted under 35 U.S.C. 154(b) by 112 days.

(21) Appl. No.: 12/620,514

(22) Filed: Nov. 17, 2009

(65) Prior Publication Data

US 2010/0292399 A1 Nov. 18, 2010

Related U.S. Application Data

(60) Provisional application No. 61/115,877, filed on Nov. 18, 2008.

(51) Int. Cl.
*H01L 29/76* (2006.01)
*H01L 29/861* (2006.01)
*C09K 19/38* (2006.01)
*C08G 65/38* (2006.01)

(52) U.S. Cl. ............... 428/1.4; 428/1.2; 257/9; 257/183; 528/219; 528/392

(58) Field of Classification Search ............... 428/1.4, 428/1.2; 524/846; 257/9, 183; 528/219, 528/392
See application file for complete search history.

(56) References Cited

U.S. PATENT DOCUMENTS

| | | | |
|---|---|---|---|
| 4,356,429 A | 10/1982 | Tang | |
| 4,539,507 A | 9/1985 | VanSlyke et al. | |
| 5,047,687 A | 9/1991 | Van Slyke | |
| 5,247,190 A | 9/1993 | Friend et al. | |
| 5,401,827 A | 3/1995 | Holmes et al. | |
| 5,454,880 A | 10/1995 | Sariciftci et al. | |
| 5,853,906 A | 12/1998 | Hsieh | |
| 5,968,674 A | 10/1999 | Hsieh | |
| 6,812,399 B2 | 11/2004 | Shaheen et al. | |
| 6,933,436 B2 | 8/2005 | Shaheen et al. | |
| 7,166,010 B2 | 1/2007 | Lamansky et al. | |
| 2005/0187411 A1 | 8/2005 | Herron et al. | |
| 2005/0247340 A1 | 11/2005 | Zeira | |
| 2006/0076050 A1 | 4/2006 | Williams et al. | |
| 2006/0078761 A1 | 4/2006 | Williams et al. | |
| 2006/0175582 A1 | 8/2006 | Hammond et al. | |
| 2006/0237695 A1 | 10/2006 | Williams et al. | |
| 2007/0065590 A1 | 3/2007 | Williams et al. | |
| 2008/0061685 A1* | 3/2008 | Chesterfield | 313/504 |
| 2008/0078437 A1 | 4/2008 | Hammond | |
| 2008/0085210 A1 | 4/2008 | Griesbach et al. | |
| 2008/0146754 A1 | 6/2008 | McCullough et al. | |
| 2008/0169451 A1 | 7/2008 | Silverman et al. | |
| 2008/0216894 A1 | 9/2008 | Hammond | |
| 2008/0223428 A1 | 9/2008 | Zeira | |
| 2008/0248313 A1 | 10/2008 | Seshadri et al. | |

FOREIGN PATENT DOCUMENTS

| | | |
|---|---|---|
| EP | 1950818 | 7/2008 |
| WO | WO 97/33193 A3 | 9/1997 |
| WO | WO 03/037844 | 5/2003 |
| WO | WO 2006/043087 | 4/2006 |
| WO | WO 2007/115540 | 10/2007 |
| WO | WO 2007/133633 | 11/2007 |
| WO | WO 2008/018931 | 2/2008 |
| WO | WO 2008/032631 | 3/2008 |

OTHER PUBLICATIONS

U.S. Appl. No. 61/043,654, filed Apr. 9, 2008, Williams et al.
International Search Report and Written Opinion mailed May 12, 2010 in corresponding Application No. PCT/US2009/064857.
Allcock, L., Contemporary Polymer Chemistry, 1981.
Billmeyer, F., Textbook of Polymer Science, $3^{rd}$ Ed., 1984.
Bredas, J. et al., Conjugated Polymers, Kluwer Academic Press, Dordrecht (1991).
Cheng, Y. et al., "Thermally Cross-Linkable Hole-Transporting Materials on Conducting Polymer: Synthesis, Characterization, and Applications for Polymer Light-Emitting Devices" Chem. Mater., vol. 20, 413-422 (2007).
Clar, E., Polycyclic Hydrocarbons vol. I and II, Academic Press, 1964.
Crivello, J., "The discovery and development of onium salt cationic photoinitiator", J. of Pol. Sci. Part A, Pol. Chem. 37, pp. 4241-4254 (1999).
Fukase, A. et al., "High-efficiency organic electroluminescent devices using iridium complex emitter and arylamine-containing polymer buffer layer," Polymers for Advanced Technologies, vol. 13, 601-604 (2002).
Harvey, R., Polycyclic Aromatic Hydrocarbons, Wiley-VCH (1996).
Iacono, S. et al., "Facile preparation of fluorovinylene aryl ether telechelic polymers with dual functionality for thermal chain extension and tandem crosslinking," Chem. Commun., pp. 4844-4846 (2006).
Jen, A et al., "High-performance blue light-emitting diode based on a binaphthyl-containing polyfluorene," vol. 76, pp. 1813-1815 (2000).
Jen, A et al., "Organic light-emitting diodes using an in situ thermally polymerized hole transporting layer," Appl. Phys. Lett., vol. 76, pp. 2985-2987 (2000).
Jen, A et al., "Thermally crosslinked hole-transporting layers for cascade hole-injection and effective electron-blocking/exciton-confinement in phosphorescent polymer light-emitting diodes," Appl. Phys. Lett., vol. 88, 093505 (2006).
Jiang, X., "Perfluorocyclobutane-based Arylamine hole-transporting materials for organic and polymer light emitting diodes," Adv. Funct. Mater., vol. 12, pp. 745-751 (2002).

(Continued)

*Primary Examiner* — Tae H Yoon
(74) *Attorney, Agent, or Firm* — Foley & Lardner LLP

(57) ABSTRACT

Oligomers and/or polymers comprising a backbone comprising arylamine and fluorinated alkyleneoxy moieties which may be crosslinked. Ink formulations and devices can be formed from the oligomers or polymers, or corresponding monomers. Doped compositions can be formed. Charge injection and transport layers can be formed. Improved stability can be achieved in organic electronic devices such as OLEDs and OPVs.

24 Claims, 11 Drawing Sheets

OTHER PUBLICATIONS

Kim, J. et al., "Optical Properties of Perfluorocyclobutane Aryl Ether Polymers for Polymer Photonic DevicesMacromolecules," Macromolecules vol. 37, pp. 5724-5731 (2004).

Kraft et al., "Electroluminescent Conjugated Polymers—Seeing Polymers in a New Light," Angew. Chem. Int. Ed., vol. 37, pp. 402-428 (1998).

Kuwano, R. et al., "Aqueous Hydroxide as a Base for Palladium-Catalyzed Amination of Aryl Chlorides and Bromides," J. Org. Chem., vol. 67, 6479-6486 (2002).

Li, Z. et al., Organic Light-Emitting Materials and Devices, CRC Press (Taylor and Francis Group, LLC), Boca Raton (2007) 1-412, 617-638.

Lim, B. et al., "Synthesis of a New Cross-Linkable Perfluorocyclobutane-Based Hole-Transport Material," Org. Lett., vol. 8, pp. 4703-4706 (2006).

Liu, M. et al., "Thermally Cross-Linkable Hole-Transporting Materials for Improving Hole Injection in Multilayer Blue-Emitting Phosphorescent Polymer Light-Emitting Diodes" Macromolecules, vol. 41, 2008, 9570-9580.

Marks, T et al., "Realization of high-efficiency/high-luminance small-molecule organic light-emitting diodes: synergistic effects of siloxane anode functionalization/hole-injection layers, and hole/exciton-blocking/electron-transport layers," App. Phys. Lett., vol. 82, pp. 331-333 (2003).

Meerholz, K. et al., "Highly efficient solution-processed phosphorescent multilayer organic light-emitting diodes based on small-molecule hosts," App. Phys. Lett., vol. 91, 103507 (2007).

Miyaura, E., Cross-Coupling Reactions: A Practical Guide (2002).

Negishi, E., Handbook of Organopalladium Chemistry for Organic Synthesis (2002).

Rothe, C., "Electrical doping is paving the way for the implementation of OLEDs in consumer electronics," Laser and Photonics Reviews vol. 1, 303-306 (2007).

Rudolf, P. et al., "Perfluorocyclobutane aromatic ether polymers. III. Synthesis and thermal stability of a thermoset polymer containing triphenylphosphine oxide," J. Appl. Pol. Sci., vol. 69, pp. 2005-2012 (1998).

Shirota, Y. et al., "Charge Carrier Transporting Molecular Materials and Their Applications in Devices," Chem. Rev. vol. 107, pp. 953-1010 (2007).

Sun, N., Organic Photovoltaics, 2005.

Smith, D. et al., "Perfluorocyclobutane Aromatic Polyethers. Synthesis and Characterization of New Siloxane-Containing Fluoropolymers", Macromolecules, vol. 29, pp. 852-860 (1996).

Smith, D. et al., "Perfluorocyclobutyl-Linked Hexa-peri-hexabenzocoronene Networks," J. Am. Chem. Soc., vol. 126, pp. 12772-12773 (2004).

Smith, D. et al., "Synthesis and Electronic Factors in Thermal Cyclodimerization of Functionalized Aromatic Trifluorovinyl Ethers," J. Am. Chem. Soc., vol. 128, pp. 7055-7064 (2006).

Smith, D. et al., "Science and technology of perfluorocyclobutyl aryl ether polymers," J. Polym. Sc. Pt. A, vol. 45, pp. 5705-5721 (2007).

Smith, D. et al., "Mixed Chromophore Perfluorocyclobutyl (PFCB) Copolymers for Tailored Light Emission," Macromolecules, vol. 40, pp. 9378-9383 (2007).

Smith, D. et al., "Synthesis and characterization of perfluorocyclobutyl (PFCB) polymers containing pendent phenylphosphine oxide," Polymer, vol. 46, pp. 6923-2932 (2005).

Smith, D. et al., "First identification of biradicals during thermal [$2\pi + 2\pi$] cyclopolymerization of trifluorovinyl aromatic ethers," Polym. Int., vol. 56, pp. 1142-1146 (2007).

Sundar, V. et al., "Fabrication and optical properties of polymeric waveguides containing nanocrystalline quantum dots," Appl. Phys. Lett., vol. 85, pp. 4469-4471 (2004).

Thompson, M. et al., "New Thermally Cross-Linkable Polymer and Its Application as a Hole-Transporting Layer for Solution Processed Multilayer Organic Light Emitting Diodes," Chem. Mat., vol. 19, pp. 4827-4832 (2007).

Wonchoba, E. et al., "Addition of phenols to perfluorovinyl ethers. Protonation and halogenation of carbanionic intermediates," J. Org. Chem., vol. 57, pp. 7014-7017 (1992).

* cited by examiner

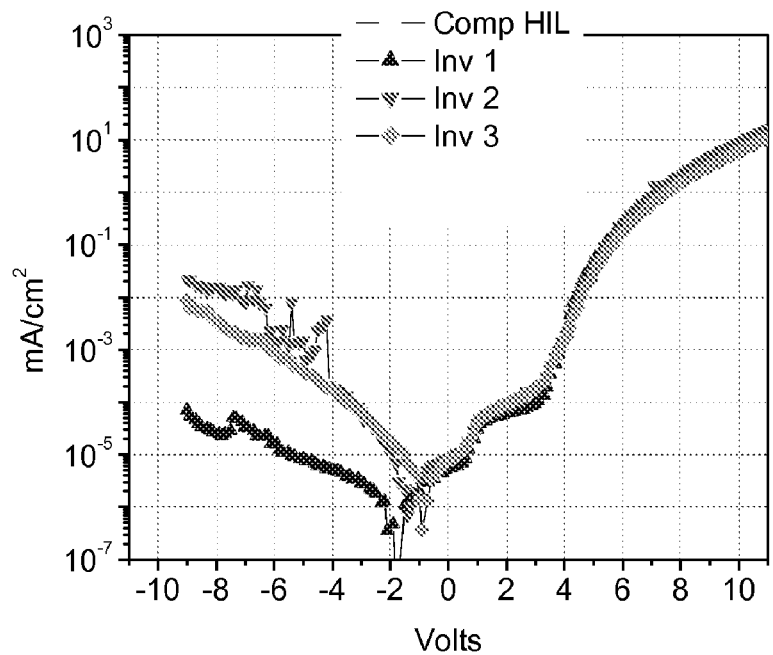
Fig. 3a JV Plot for Inv 1-3 and Comp HIL
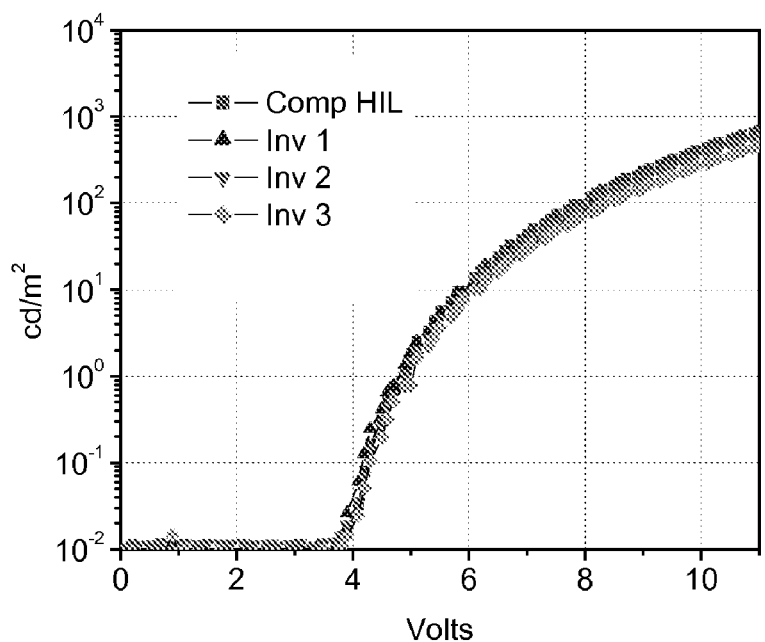
Fig. 3b LV Plot for Inv 1-3 and Comp HIL

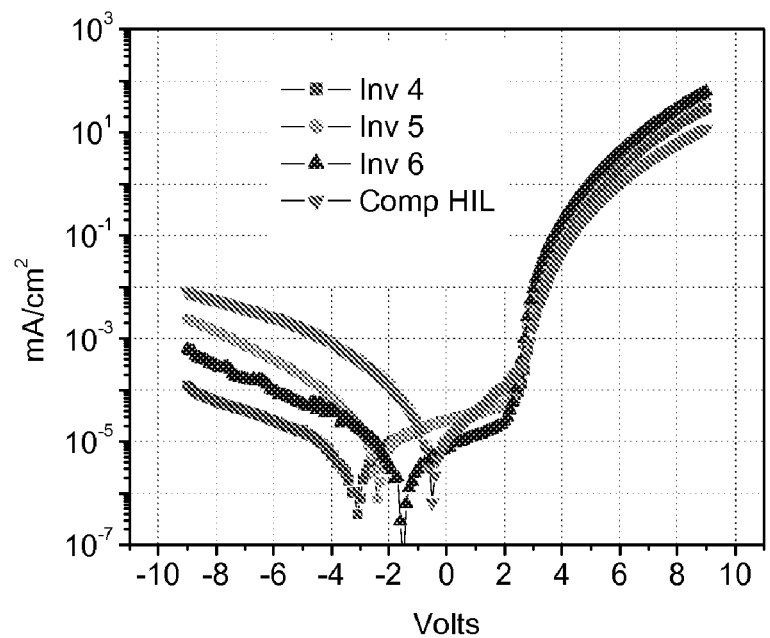
Fig. 10a JV Plot for Inv 4-6 and Comp HIL
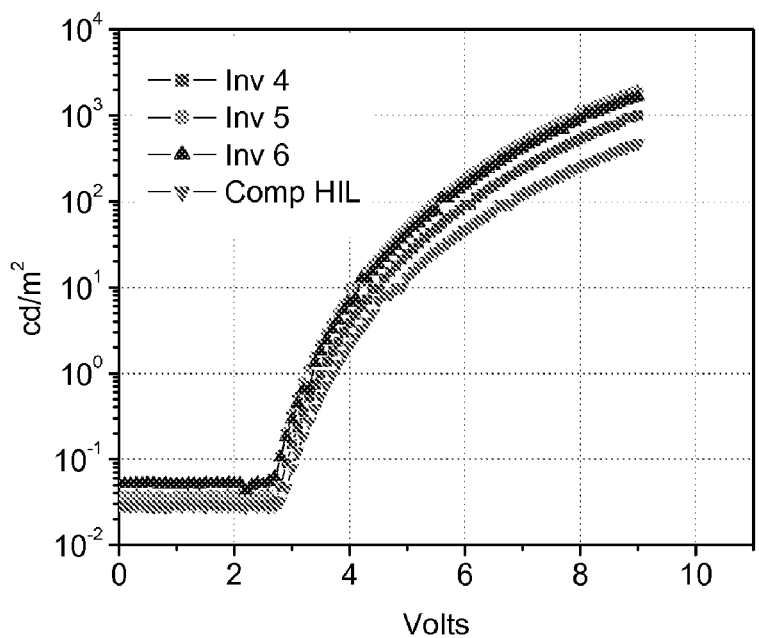
Fig. 10b LV Plot for Inv 4-6 and Comp HIL

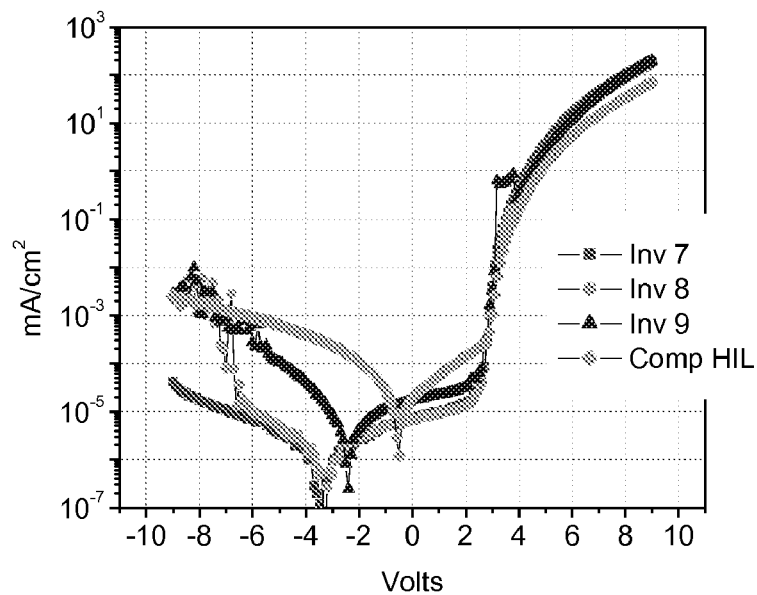
Fig. 11a JV Plot for Inv 7-9 and Comp HIL
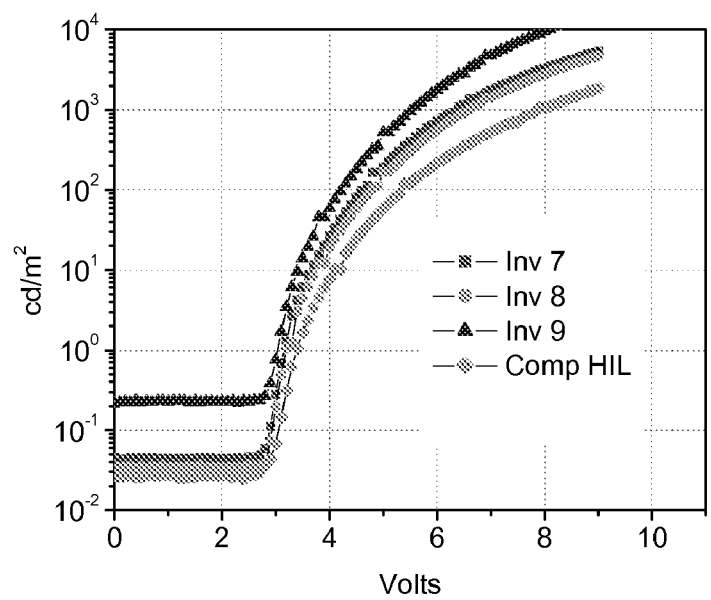
Fig. 11b LV Plot for Inv 7-9 and Comp HIL

AMINOBENZENE COMPOSITIONS AND RELATED DEVICES AND METHODS

RELATED APPLICATIONS

This application claims priority to U.S. provisional application 61/115,877 filed Nov. 18, 2008, which is hereby incorporated by reference in its entirety.

BACKGROUND

A need exists for improving the performance of a variety of electronic devices such as, for example, organic light emitting devices such as organic light emitting diodes (OLEDs) as well as photovoltaic devices such as organic photovoltaics (OPVs). One way this need is met is through development of new materials for these devices that enhance device output and prolong device lifetime. A particularly promising approach lies in the development of new materials for device layers such as the hole injection, hole transport, and hole extraction layers.

In particular, improvements in technologies for hole injection and/or hole transport in these devices is especially desirable. State of the art organic electronic devices generally still can benefit from hole injection layers (HILs) and/or hole transport layers (HTLs) within the device to optimize charge flow through the device, and separation or recombination of electrons and holes. Hole injection layers and hole transport layers can present difficult problems, however, because of the solubilities of the component materials (or lack thereof) in processing solvents, and because of the dopants and/or acids needed for HIL performance. Dopants and acids should be chosen judiciously to minimize their contributions to device operation (e.g., efficiency and degradation).

Further, a need is recognized to exist wherein the hole injection and/or hole transport layer components are processable from selected solvents such as, for example, non-aqueous and/or aprotic high-purity solvent in order to minimize deleterious effects on device operation. In addition, a need also exists to develop layers that are compatible with the deposition of subsequent layers by vapor or solution processes.

SUMMARY

Compositions for use in, for example, hole transporting layers (HTLs) or hole injection layers (HILs) are provided, as well as methods of making the compositions and devices fabricated from the compositions.

The compositions can comprise at least one semiconductive organic material, and an optional dopant, and can be substantially free, or totally free, of an insulating matrix component. The compositions can, for example, produce improved HILs and HTLs that, when incorporated into electronic devices such as OLEDs or OPVs, can lead to increases in the performance of the devices.

One embodiment provides a composition comprising a polymeric or oligomeric backbone comprising at least one repeat moiety comprising at least one arylamine, and at least one repeat moiety comprising at least one fluorinated alkyleneoxy.

One embodiment provides, for example, a composition comprising a polymeric or oligomeric backbone comprising at least one arylamine repeat moiety and at least one fluorinated alkyleneoxy repeat moiety.

Another embodiment provides an oligomer or polymer comprising repeat units represented by

    (I)

    (II)

wherein,
Ar$^1$ comprises or is an arylamine,
Ar$^2$ comprises an aryl, and
R$^1$ and R$^2$ are independently selected from C$_1$-C$_{10}$ fluorinated alkylenes.

Another embodiment provides a method of making an oligomer or polymer comprising co-polymerizing a first monomer represented by:

$$HO—Ar^4—OH \qquad (X)$$

with a second monomer represented by:

$$R^5—O—Ar^5—O—R^6 \qquad (XII)$$

wherein Ar$^4$ and Ar$^5$ are independently chosen from an aryl moiety or an arylamine moiety, such that at least one of Ar$^4$ and Ar$^5$ being an arylamine; and R$^5$ and R$^6$ independently represent a fluorinated C$_1$-C$_{10}$ alkylene.

Yet another embodiment provides an oligomer or polymer formed by co-polymerizing a first monomer represented by:

$$HO—Ar^4—OH \qquad (X)$$

with a second monomer represented by:

$$R^5—O—Ar^5—O—R^6 \qquad (XII)$$

wherein Ar$^4$ and Ar$^5$ are independently chosen from an aryl moiety or an arylamine moiety, such that at least one of Ar$^4$ and Ar$^5$ being an arylamine; and R$^5$ and R$^6$ independently represent a fluorinated C$_1$-C$_{10}$ alkylene.

Yet another embodiment provides a composition comprising an oligomer or polymer comprising repeat units represented by:

    (I)

    (II)

wherein, Ar$^1$ is an arylamine, Ar$^2$ is an aryl, and R$^1$ and R$^2$ are independently selected from C$_1$-C$_{10}$ fluorinated alkyls; and at least one solvent.

Still another embodiment provides a device comprising a layer comprising an oligomoer or polymer comprising repeat units represented by:

    (I)

    (II)

wherein, Ar$^1$ is an arylamine, Ar$^2$ is an aryl, and R$^1$ and R$^2$ are independently selected from C$_1$-C$_{10}$ fluorinated alkyl.

Another embodiment provides a composition comprising: (i) at least one arylamine, and (2) at least one fluorovinylether unit covalently linked to the arylamine. The composition can be a monomer, oligomer, or polymer. Another embodiment provides a composition consisting essentially of: (i) at least one arylamine, and (2) at least one fluorovinylether unit covalently linked to the arylamine.

Another embodiment provides a composition comprising a polymeric or oligomeric backbone comprising at least one repeat moiety adapted to provide hole transport and at least one fluorinated alkyleneoxy repeat moiety.

One embodiment provides a method comprising: reacting at least one arylamine comprising at least two secondary amine moieties with at least one arylbromide, wherein the arylbromide comprises alkylenoxy units, to form a arylamine monomer comprising alkyleneoxy units, wherein the reaction is carried out with use of an organometallic complex.

One advantage of some embodiments is in providing a polymer with better operational stability.

Another advantage of some embodiments is in providing a polymer which facilitates charge injection into device layers.

Another advantage of some embodiments is in providing polymers compatible with orthogonal solvents for preparing solution processed device layers.

Yet another advantage of some embodiments is in providing a relatively simple method of making a polymer for hole injection or hole extraction layer.

Still another advantage of some embodiments is in providing materials which assist in reducing the leakage current for OPV devices.

BRIEF DESCRIPTION OF FIGURES

FIGS. 3a and 3b are IVL measurements for a comparative hole injection layer and a hole injection layer according to an embodiment, respectively.

FIG. 10 a,b show IVL measurement for devices 4, 5, 6 and comparative example.

FIG. 11a, b show IVL measurement for devices 7, 8, 9 and comparative example.

DETAILED DESCRIPTION

Introduction

Figure 1:
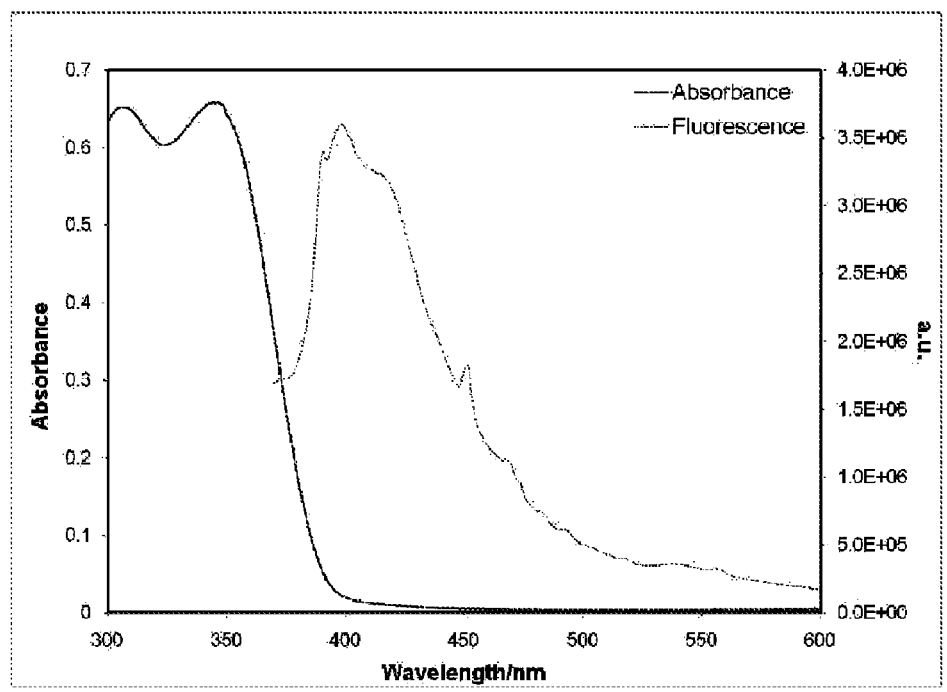
FIG. 1 shows absorbance and fluorescence spectra of thin films of poly(TPD-TFVBPA) on a glass substrate.

The term "TPD" as used herein refers to 4,4'-bis(m-tolyphenylamino)biphenyl.

The term "poly(TPD-TFVBPA)" as used herein refers to the polymer prepared as prepared below in working example 1.

The term "TPD-TFV" as used herein refers to the compound as prepared below in working example 2.

The term "poly(nap-TPD-TFV)" as used herein refers to the polymer as prepared below in working example 3.

All references cited herein are incorporated by reference in their entireties.

Compositions provided herein can comprise at least one semiconductive component, and an optional dopant, and can be substantially free of an insulating matrix component. The compositions can be used to form improved HTLs or HILs that, when incorporated into electronic devices such as OLEDs or OPVs, can result in increased device performance. For example, the compositions can include ink formulations that can be used to form HILs in OLEDs. OLEDs constructed with the compositions can exhibit increases in efficiency and brightness. The present compositions thus can provide an improved hole injection technology that can be used in applications involving organic electroluminescence, in particular, in OLEDs and other lighting displays and/or applications.

In the compositions for at least some embodiments, the semiconductive component when present as either an HIL or HTL layer in a device, can permit charge injection to take place throughout the bulk of the layer rather than at the surface of the layer.

The compositions can also contain a dopant that can function as a doping agent for compositions of one or more semiconducting polymers. Doping of the semiconducting materials and polymer can enable rapid charge transport through the bulk of the present compositions when incorporated into an organic electronic device, increasing the performance of the device. The semiconductive doped polymers of the compositions can produce HILs or HTLs having higher conductivities, which lower the series resistance of organic electronic devices. This is in contrast to other hole injection technologies which can produce HILs or HTLs having much lower conductivities (and, as a consequence, devices with higher series resistance).

In some embodiments, the compositions can produce HILs or HTLs that are substantially transparent to visible light, even if the thickness of the layer is higher than usual, for example, on the order of about 60 nm to about 200 nm. For example, the HIL or HTL can transmit about 85% to about 90% or greater (i.e., % T>85-90%) of light having a wavelength of about 400-800 nm. Thus, an additional advantage for at least some embodiments can be the formation of substantially transparent HILs or HTLs having moderately high thicknesses. Thick HILs or HTLs can also be used to eliminate shorts in semiconductor devices without adversely impacting operating voltage.

More particularly, the present embodiments include, for example, aminobenzene monomers, oligomers, and polymers (including co-polymers), methods of making the same and compositions and devices formed using the monomers, oligomers, and polymers. The polymers can comprise at least one arylamine moiety and at least one halogenated alkyleneoxy moiety such as fluorinated alkyleneoxy moiety. A method of making the oligomers or polymers can comprise, for example, co-polymerizing a monomer comprising hydroxyl groups with a monomer comprising halogenated or fluorinated alkyleneoxy groups. The oligomers or polymers can be used in ink compositions and further used to form functional layers in various devices.

Prior U.S. patent publications related to semiconductive and conjugated polymers, including polythiophenes and regioregular polythiophenes, hole injection and hole transport, and organic electronic devices include, for example:

20080248313 Sulfonation of conducting polymers and OLED, photovoltaic, and ESD devices
20080223428 All printed solar cell array
20080216894 Quantum Dot Photovoltaic Device
20080169451 Conductive Block Copolymers
20080146754 Universal Grignard Metathesis Polymerization
20080085210 Decontamination of filtration media for respiration
20080078437 Solar Farms Having Ultra-Low Cost OPV Modules
20070065590 Latent doping of conducting polymers
20060237695 Copolymers of soluble poly(thiophenes) with improved electronic performance
20060175582 Hole injection/transport layer compositions and devices 20060118901 Heteroatomic regioregular poly(3-substitutedthiophenes) as thin film conductors in diodes which are not light emitting or photovoltaic 20060078761 Heteroatomic regioregular poly(3-substitutedthiophenes) in electroluminescent devices 20060076050 Heteroatomic regioregular poly(3-substitutedthiophenes) for photovoltaic cells 20050247340 All printed solar cell array.

Polymers and copolymers are generally known in the art. See, for example, Billmeyer, *Textbook of Polymer Science*, 3rd Ed., 1984; Allcock, Lampe, *Contemporary Polymer Chemistry*, 1981. Polymers and copolymers can comprise polymeric and copolymeric backbones which further comprise atoms and side groups bonded to the backbone.

The polymers and copolymers can be soluble, linear molecules. The can comprise repeat moieties. For example, in one embodiment, a co-polymer comprises a backbone comprising at least one arylamine repeat moiety and at least one fluorinated alkyleneoxy repeat moiety. The moieties can be alternating. Oligomers can be made. Crosslinked materials can be made including lightly crosslinked and heavily crosslinked materials. Network materials can be made.

Oligomers are known in the art and can be lower molecular weight forms of polymers. Oligomers can be linear or crosslinked. Network oligomers can be prepared. Oligomer molecular weight can be, for example, 1,000 g/mol or less, or 750 g/mol or less (Mn).

Hole Transport/Arylamine Repeat Moiety

Hole transport materials are known in the art including, for example, arylamine materials and compounds. Arylamine repeat moieties are known in the art. See, for example, Lim et al., *Organic Letters*, 2006, 8, 21, 4703-4706; Fukase et al., *Polymers for Advanced Technologies*, 13, 601-604 (2002). Shirota, Y. et al., *Chem. Rev.* 107, 2007, 953-1010; Z. Li and H. Meng, Eds., *Organic Light-Emitting Materials and Devices*, CRC Press (Taylor and Francis Group, LLC), Boca Raton (2007) and references therein. The arylamine moieties can each comprise at least one nitrogen atom and at least one benzene ring. As a non-limiting example, they can comprise one benzene ring bonded to a nitrogen atom; two benzene rings bonded to a nitrogen atom; or three benzene rings bonded to a nitrogen atom. The repeat moiety can be adapted to provide hole injection and/or hole transport properties.

In addition, hole transport compositions and repeat moieties may additionally be selected to include but are not limited to thiophenes, pyrroles, aryloxy and organometallic complex moieties. See, for example, Shirota, Y. et al., *Chem. Rev.* 107, 2007, 953-1010; Z. Li and H. Meng, Eds., *Organic Light-Emitting Materials and Devices*, CRC Press (Taylor and Francis Group, LLC), Boca Raton (2007) and references therein.

As a non-limiting example, the arylamine moiety can comprise at least one triarylamine.

As yet another non-limiting example, the arylamine moiety can comprise a bistriarylamine, such as, but not limited to, N,N-diphenylbenzeneamine.

The benzene ring(s) may be bonded to at least one other benzene ring through a direct covalent bond, a covalent bond through at least one carbon atom or a covalent bond through an oxygen atom.

The benzene ring(s) may be fused with another benzene ring through one or two carbon atoms shared between the rings. Two or more rings can be fused together.

The benzene rings can be substituted or unsubstituted. As a non-limiting example, they can be substituted with one or more $C_1$-$C_{10}$ alkyl, perfluoroalkyl, thioalkyl, alkoxy, alkylaryl, arylalkyl, aryloxy, heteroaryl, cyano, halo and alkylthio groups, or a combination thereof.

Arylamines are also described in, for example, U.S. Pat. No. 7,166,010; WO 2003037844; and WO 2008032631, which are hereby incorporate by reference in their entirety.

Spacer/Fluorinated Alkyleneoxy Repeat Moieties

A moiety can help space the hole transport functionality. This moiety can be different from the arylamine moiety described above. Spacers such as halogenated and fluorinated alkyleneoxy repeat moieties are known in the art. See, for example, Iacono et al., *Chem. Commun.*, 2006, 4844-4846; Babb et al., *Macromolecules*, 1996, 29, 852-860; Smith et al., *Polym. Int.*, 2007, 56, 1142-1146; Smith et al., *J. Am. Chem. Soc.*, 2004, 126, 12772-12773; Kim et al., *Org. Lett.*, 2006, 8, 4703-4706. Rudolf et al., *J. Appl. Pol. Sci.*, 1998, 69, 2005-2012; Kim et al., *Macromolecules*, 2004, 37, 5724-5731; Smith et al., *Macromolecules*, 2007, 40, 9378-9383; Smith et al., *J. Am. Chem. Soc.*, 2006, 128, 7055-7064; Sundar et al., *Appl. Phys. Lett.*, 2004, 85, 4469-4471; Smith et al., *J. Polym. Sc. Pt. A*, 2007, 45, 5705-5721; Smith et al., *Polymer*, 2005, 46, 6923-2932; Smith et al., *Chem. Comm.*, 2006, 4844-4846; Wonchoba et al., *J. Org. Chem.*, 1992, 57, 7014-7017; Jen et al., *Appl. Phys. Lett.*, 2006, 88, 093505; Jen et al. Adv. Funct. Mat., 2002, 12, 745-751; Jen et al., *Appl. Phys. Lett.*, 2000, 76, 1813-1815; Jen et al., *Appl. Phys. Lett.*, 2000, 76, 2985-2987. Fluorinated alkyleneoxy repeat moieties can comprise at least one fluorine atom, at least one oxygen atom, and at least one alkylene moiety which can be a $C_1$-$C_{10}$ alkylene. More preferably, the alkylene moiety can be a $C_1$-$C_5$ alkylene, such as, but not limited to an ethylene. The $C_1$-$C_{10}$ alkylene can be linear, branched or cyclic.

The $C_1$-$C_{10}$ alkylene can be fluorinated with at least one fluoro, chloro, bromo or iodo group, or combination thereof. Preferably, the alkylene moiety is fluorinated with at least one fluoro group such as, for example, forming a trifluoroethylene moiety. Preferably, the alkylene moiety is perflourinated.

The fluorinated alkoxy moieties, which can be converted to fluorinated alkyleneoxy, can further comprise at least one aryl, arylalkyl, haloarylalkyl, diarylamine, or a triarylamine. As a non-limiting example, the aryl moiety is N,N-diphenylbenzeneamine. The benzene ring(s) of the aryl moiety can be covalently bonded to the alkyl portion or to the oxygen atom. Preferably the benzene ring of the aryl moiety is bonded to the oxygen atom of the fluorinated alkoxy moiety.

In one embodiment, the repeat moieties, arylamine and fluorinated alkyleneoxy are the only repeat units. In other embodiments, the copolymer can consist of or can consist essentially of these two types of repeat moieties. If desired, the arylamine can be replaced by another hole transport moiety.

Vinyl ether, fluorinated vinyl ether, and perfluorinated vinyl ether moieties can be used including both in polymerized or unpolymerized forms, and combinations thereof.

Oligomer/Polymer/Copolymer Structures

The oligomers, polymers, and co-polymers can be further described with structures as follows. For example, in one embodiment, they comprise repeat units represented by

(I)

and

(II)

wherein, $Ar^1$ comprises an arylamine, $Ar^2$ comprises an aryl, and $R^1$ and $R^2$ are independently selected from $C_1$-$C_{10}$ fluorinated alkylenes.

The repeat units (I) and (II) can be alternating.

More particularly, $Ar^1$ can comprise or be a triarylamine where the benzene rings are optionally substituted. As a non-limiting example, $Ar^1$ can be represented by

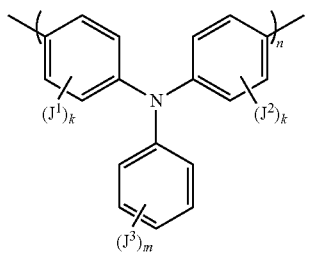

(III)

wherein, $J^1$, $J^2$ and $J^3$ are independently selected from hydrogen, $C_1$-$C_{10}$ alkyl, perfluoroalkyl, thioalkyl, alkoxy, alkylaryl, arylalkyl, aryloxy, heteroaryl, cyano, halo and alkylthio groups; k is an integer from 1 to 4; m is an integer from 1 to 5; and n is an integer from 1 to 5.

In a particular example $Ar^1$ can be represented by

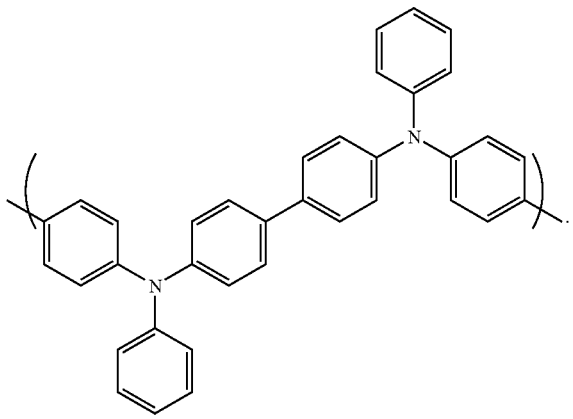

(IV)

$Ar^2$ can comprise or be, for example, an aryl, arylalkyl, haloarylalkyl, diarylamine or a triarylamine. For example, $Ar^2$ can be an aryl comprising a benzene ring or at least two benzene rings covalently bonded to each other. $Ar^2$ can be an arylene. In a non-limiting example, $Ar^2$ is represented by

(V)

wherein z is an integer from 1 to 5.

In addition, $Ar^2$ can be an aryl comprising a polycyclic aromatic ring or an aryl comprising a substituent having 2-10 carbon atoms. The polycyclic aromatic ring can have, for example, two or more rings fused together. In a non-limiting example, $Ar^2$ can be represented by

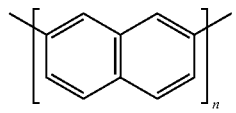

(VI)

wherein n is an integer from 1 to 5. Isomeric forms of the linkages can be used.

$Ar^2$ can be a triarylamine. The structures for $Ar^2$ also can be the structures for $Ar^1$.

$Ar^2$ can be an arylalkyl or a haloarylalkyl. In a non-limiting example, $Ar^2$ can be represented by:

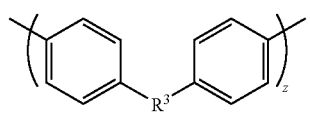

(VI-B)

wherein, $R^3$ is an optionally fluorinated $C_1$-$C_{10}$ alkyl, such as an optionally fluorinated $C_1$-$C_{10}$ alkyl, and z is an integer from 1 to 5. $R^3$ may be a linear, branched or cyclic alkyl.

As another non-limiting example, $Ar^2$ can be represented by:

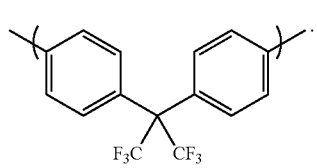

(VII)

In the repeat unit represented by structure (II), $R^1$ and $R^2$ can be, for example, independently selected from $C_1$-$C_{10}$ alkyl, such as $C_1$-$C_{10}$ fluoroalkyl. In a non-limiting example, $R^1$ and $R^2$ are trifluoroethylene.

In a particular embodiment, a co-polymer can comprise a repeat unit represented by

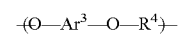

(VIII)

wherein, $Ar^3$ can be an arylamine, and $R^4$ can be a $C_1$-$C_{10}$ fluorinated alkylene.

For example, $Ar^3$ can be a diaryl or a triaryl amine. The structures for $Ar^3$ also can be the structures described above for $Ar^1$ and/or $Ar^2$.

Isomers of these embodiments can be also used.

Monomer Synthesis

Certain monomers can be commercially obtained while others may be synthesized. Non-limiting examples of synthetic monomers are provided below.

Methods known in the art, including organic synthesis and polymer arts, can be used to prepare monomers comprising polymerizable or reactive functional groups, and to couple monomers together to form polymers. See, for example, *March's Advanced Organic Chemistry*, 6th Ed, 2007.

Monomers and reactions, including nucleophilic addition reactions, involving fluorinated unsaturated compounds and polymers are known in the art. See, for example, *Synthetic Fluorine Chemistry*, Ed. Olah, 1992.

Methods are known in the art for synthetically accessing and utilizing the fluorinated alkyleneoxy repeat moieties. See, for example, Iacono et al., *Chem. Commun.*, 2006, 4844-4846; Babb et al., *Macromolecules*, 1996, 29, 852-860; Smith et al., *Polym. Int.,* 2007, 56, 1142-1146; Smith et al., *J. Am. Chem. Soc.,* 2004, 126, 12772-12773; Kim et al., *Org. Lett.,* 2006, 8, 4703-4706. Rudolf et al., *J. Appl. Pol. Sci.,* 1998, 69, 2005-2012; Kim et al., *Macromolecules,* 2004, 37, 5724-5731; Smith et al., *Macromolecules,* 2007, 40, 9378-9383; Smith et al., *J. Am. Chem. Soc.,* 2006, 128, 7055-7064; Sundar et al., *Appl. Phys. Lett.,* 2004, 85, 4469-4471; Smith et al., *J. Polym. Sc. Pt. A,* 2007, 45, 5705-5721; Smith et al., *Polymer,* 2005, 46, 6923-2932; Smith et al., *Chem. Comm.,* 2006, 4844-4846; Wonchoba et al., *J. Org. Chem.,* 1992, 57, 7014-7017.

Additionally, methods are known in the art for conducting bond forming cross-coupling/amination reactions. See for example, *Cross-Coupling Reactions: A Practical Guide,* Ed. Miyaura, 2002; *Handbook of Organopalladium Chemistry for Organic Synthesis,* Ed. Negishi, 2002. Kuwano et al., *J. Org. Chem.,* 2002, 67, 6479-6486.

One first monomer can be adapted to provide a hole transporting function. One second monomer can be used to provide a spacer function to separate and connect hole transport moieties. Monomers can be selected to include a broad range of basic moieties with appropriate hydroxyl or fluorinated alkyleneoxy substituents to be useful in this invention. See, for example, *Polycyclic Aromatic Hydrocarbons,* Harvey, R. G., Wiley-VCH, 1996; *Polycyclic Hydrocarbons Vol. I and II,* Clar, E, Academic Press, 1964.

Monomers can be prepared or obtained which provide the arylamine repeat moiety in the resulting polymer.

Generally, one set of monomers can comprise a hole transport moiety and two hydroxyl end groups, such as, but not limited to, hydroxylaryl groups or aminohydroxylaryl groups. The hole transport moiety can comprise at least one aryl group. For example, the hole transport functionality can comprise 1-10 aryl groups.

Non-limiting examples of such monomers are shown below,

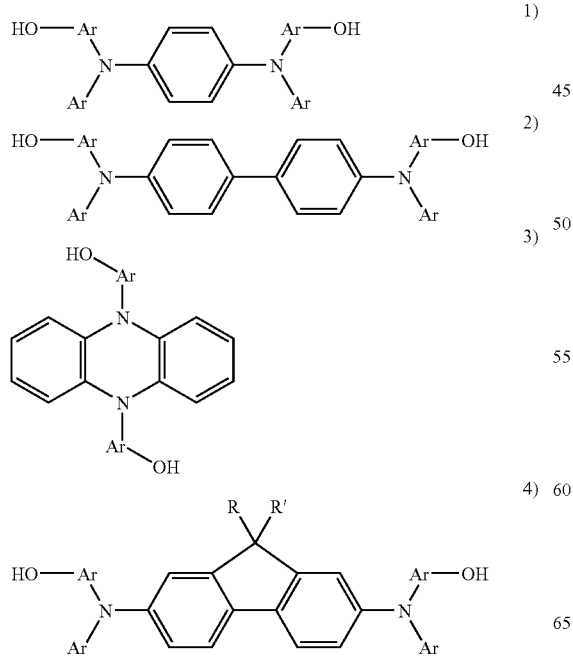

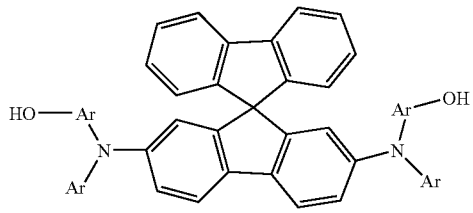

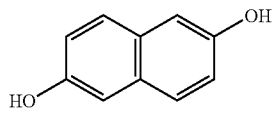

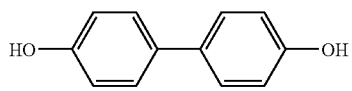

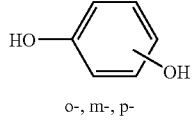

o-, m-, p-

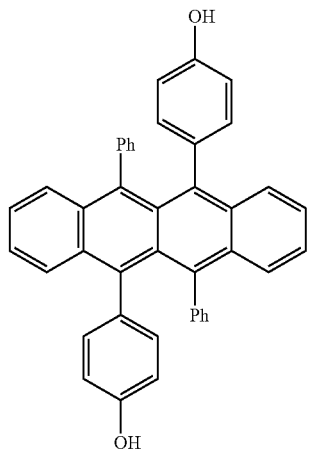

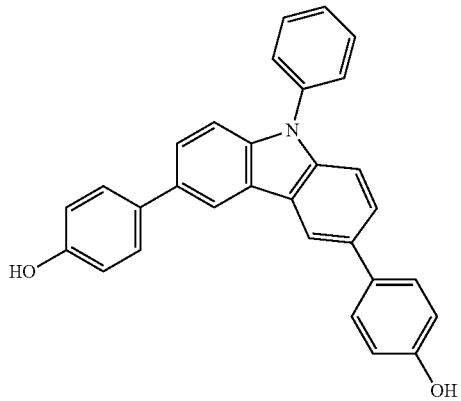

11)
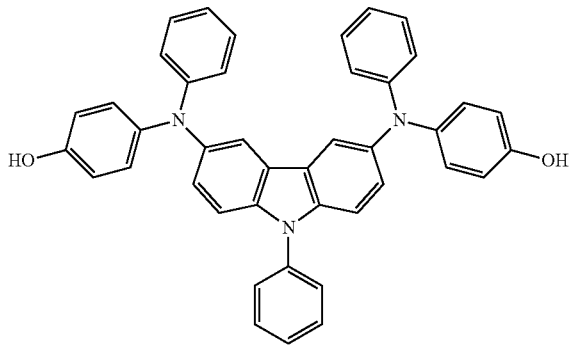

12)
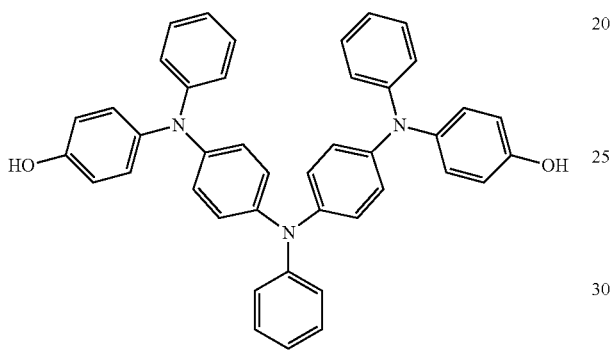

wherein Ar is independently selected from, for example, aryl groups such as benzene, naphthalene, biphenyl, and may be optionally substituted, and R is alkyl or ethyleneoxy and may be optionally substituted.

The substitutions may be selected to provide, for example, desired energetic (HOMO-LUMO, triplet, singlet), mobility and thermodynamic properties for optimal handling, efficiency, and/or operational lifetime.

Additionally, monomers can be prepared or obtained which provide the fluorinated alkylenoxy repeat moiety in the resulting polymer. For example, another set of monomers can include arylamines which include fluorinated alkyleneoxy group(s). Generally, these monomers can comprise a spacer moiety and two, three, or more trifluorovinyloxy end groups.

The spacer moiety can comprise at least one aryl group. For example, the spacer moiety can comprise 1-10 aryl groups.

Non-limiting examples of such monomers are shown below,

13)
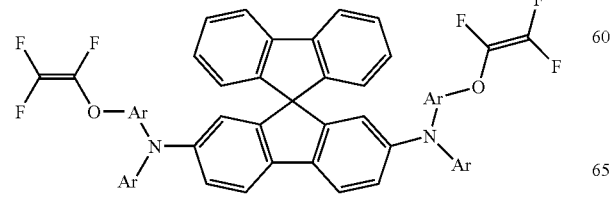

14)
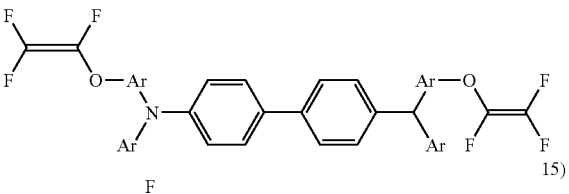

15)
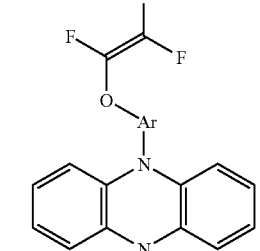

16)
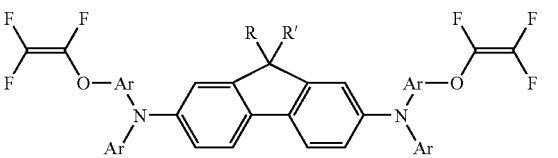

17)
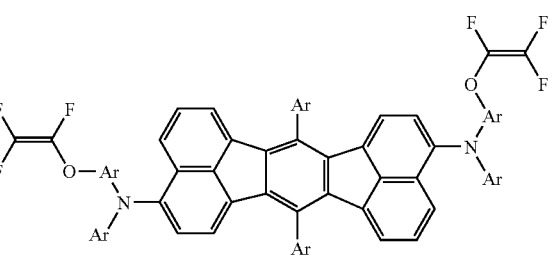

18)
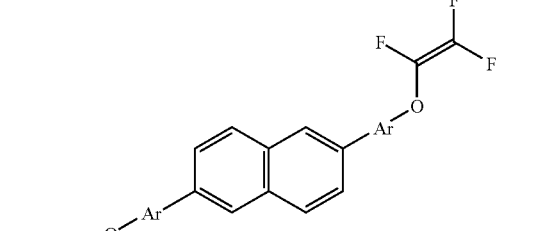

19)
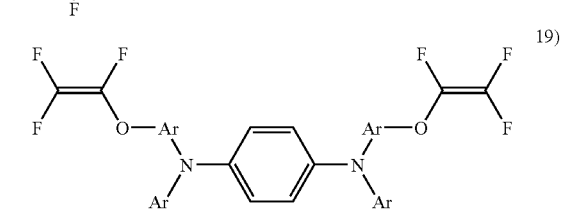

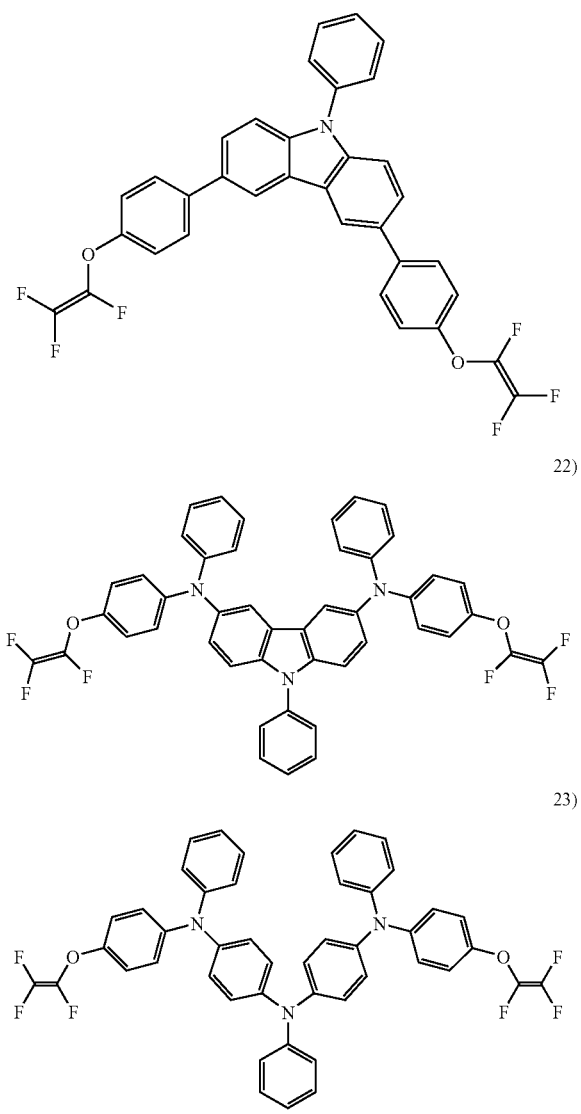

an A-B copolymer. Or alternatively, A and B can be combined before polymerization to form A-B, and then A-B can be polymerized.

Additionally, monomers can be tri-, tetra-, or higher functional so that networks can form.

In one embodiment, the monomers can be adapted to comprise phenolic or hydroxyl groups and/or trifluorovinylether groups, which can add together in a polymerization reaction.

In one embodiment, a monomer comprises reactive fluorinated alkenes.

Fluorinated alkenes can react with each other to provide coupling for oligomerization or polymerization including, for example, cycloaddition reactions. For example, trifluorovinyl ether-containing compounds can be useful reactive monomers that undergo thermal cyclopolymerization to afford perfluorocyclobutane (PFCB) polymers.

One embodiment provides a method comprising: reacting at least one arylamine comprising at least two secondary amine moieties with at least one arylbromide, wherein the arylbromide comprises alkylenoxy units, to form a arylamine monomer comprising alkyleneoxy units, wherein the reaction is carried out with use of an organometallic complex such as, for example, zero valent palladium complex such as $Pd_2(dba)_3$. See, for example, working example 2; see in contrast comparative example 2A. The reaction can be carried out under phase transfer conditions with use of combinations of water, organic solvent (e.g., toluene), and phase transfer catalyst. Strong base can be used such as, for example, KOH. The arylamine comprising at least two secondary amine moieties can be, for example, N,N'-diphenylbenzidine.

Polymer Synthesis

Polymer synthesis methods are known in the art. See, for example, Billmeyer, *Textbook of Polymer Science*, 3$^{rd}$ Ed., 1984; Allcock, Lampe, *Contemporary Polymer Chemistry*, 1981. Examples include, but are not limited to, step growth, condensation polymerization, addition polymerization, free-radical polymerization, cationic polymerization, anionic polymerization and coordination polymerization. In some embodiments, the polymerization reaction includes the reaction of a compound comprising a hydroxyl group, such as a hydroxyaryl group, with a compound comprising fluorinated alkyleneoxy groups. These methods can be also used to produce oligomers as known in the art.

In one embodiment, a first monomer comprising at least two hydroxyl groups is co-polymerized with a second monomer comprising at least two fluorinated alkyleneoxy groups. Preferably, the second monomer comprises at least two trifluoroethyleneoxy groups.

In another embodiment a co-polymer or oligomer is formed by co-polymerizing a first monomer represented by:

$$HO—Ar^4—OH \qquad (X)$$

with a second monomer represented by:

$$R^5—O—Ar^5—O—R^6 \qquad (XII)$$

wherein $Ar^4$ and $Ar^5$ are independently chosen from an aryl moiety or an arylamine moiety, such that at least one of $Ar^4$ and $Ar^5$ is an arylamine, and $R^5$ and $R^6$ independently represent a fluorinated $C_1$-$C_{10}$ alkylene.

Monomers can be bifunctional so that linear, soluble oligomers or polymers can be prepared. For example, an A monomer can be adapted to react with a B monomer to form Ar⁴ can be represented by

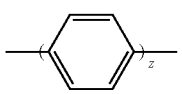
(V)

wherein z is an integer from 1 to 5.

Alternatively, Ar⁴ can be represented by

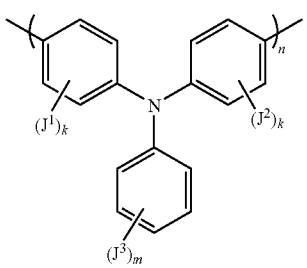
(III)

wherein, $J^1$, $J^2$ and $J^3$ are independently selected from hydrogen, $C_1$-$C_{10}$ alkyl, perfluoroalkyl, thioalkyl, alkoxy, alkylaryl, arylalkyl, aryloxy, heteroaryl, cyano, halo and alkylthio groups; k is an integer from 1 to 4; m is an integer from 1 to 5; and n is an integer from 1 to 5.

As yet another alternative, Ar⁴ can be represented by

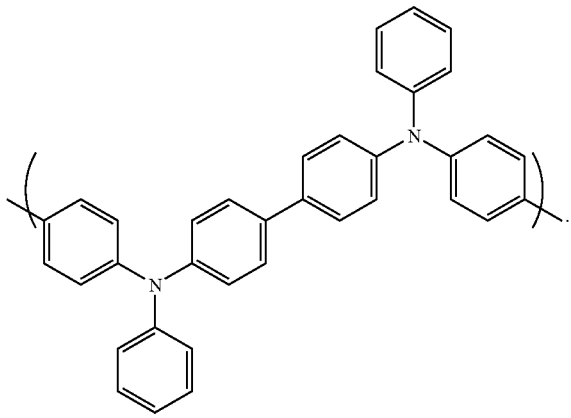
(IV)

In the second monomer, Ar⁵ can be represented by

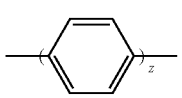
(V)

where z is an integer from 1 to 5.

Alternatively, Ar⁵ can be represented by

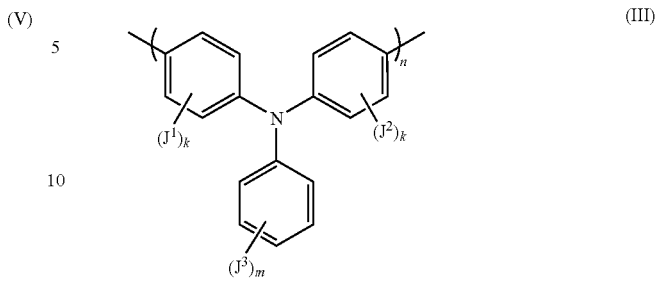
(III)

wherein, $J^1$, $J^2$ and $J^3$ are independently selected from hydrogen, $C_1$-$C_{10}$ alkyl, perfluoroalkyl, thioalkyl, alkoxy, alkylaryl, arylalkyl, aryloxy, heteroaryl, cyano, halo and alkylthio groups; k is an integer from 1 to 4; m is an integer from 1 to 5; and n is an integer from 1 to 5.

As yet another alternative, Ar⁵ can be represented by

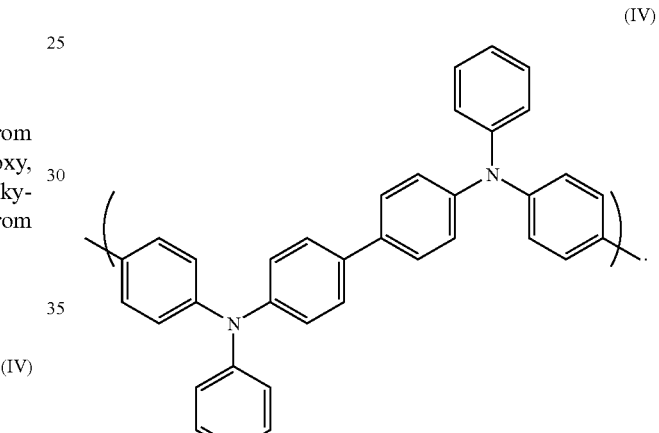
(IV)

As still another alternative, Ar⁵ can be represented by

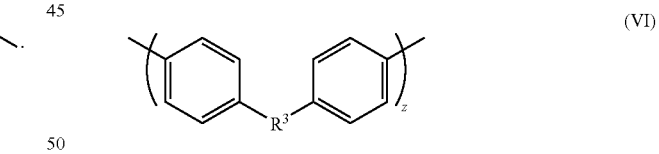
(VI)

wherein $R^3$ can be an optionally fluorinated $C_1$-$C_{10}$ alkyl, such as an optionally fluorinated $C_1$-$C_{10}$ alkyl, and z is an integer from 1 to 5. $R^3$ may be a linear, branched or cyclic alkyl.

$R^5$ and $R^6$ can be independently selected from fluorinated alkylenes such as, but not limited to, fluorinated $C_1$-$C_{10}$ alkylenes. Preferably, $R^5$ and $R^6$ are independently selected from fluorinated $C_1$-$C_{10}$ alkylene, such as trifluoroethylene.

In a particular embodiment one monomer is used to form a polymer. The monomer can comprise at least one hydroxyarylamine moiety and at least one fluorinated $C_1$-$C_{10}$ alkyleneoxy moiety.

In one embodiment, a polymer is formed by polymerizing a monomer represented by:

$$HO-Ar^6-O-R^7 \quad (XIII)$$

wherein $Ar^6$ is an arylamine and $R^7$ is a fluorinated $C_1$-$C_{10}$ alkyleneoxy.

These monomers may be commercially obtained or synthesized using methods known in organic chemistry.

Polymerization can be carried out in various solvents. Examples include Dimethyl sulfoxide, tetramethylenesulfoxide, dimethylformamide, dimethylacetamide, N-methylpyrrollidinone, tetrahydrofuran, dioxane and acetonitrile, and combinations thereof.

Polymerization can be carried out in the presence of various catalysts. Examples include sodium tert-butoxide, sodium methoxide, potassium tert-butoxide and potassium methoxide.

Representative polymers resulting from such polymerization include, for example:

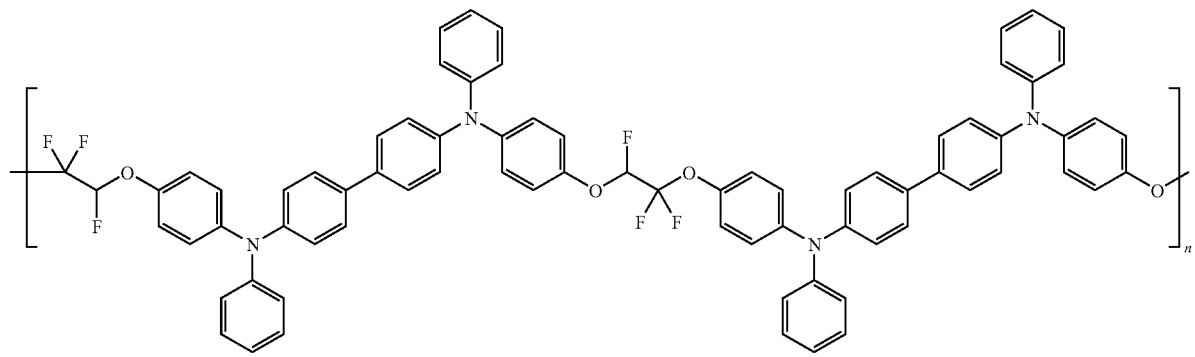

24)

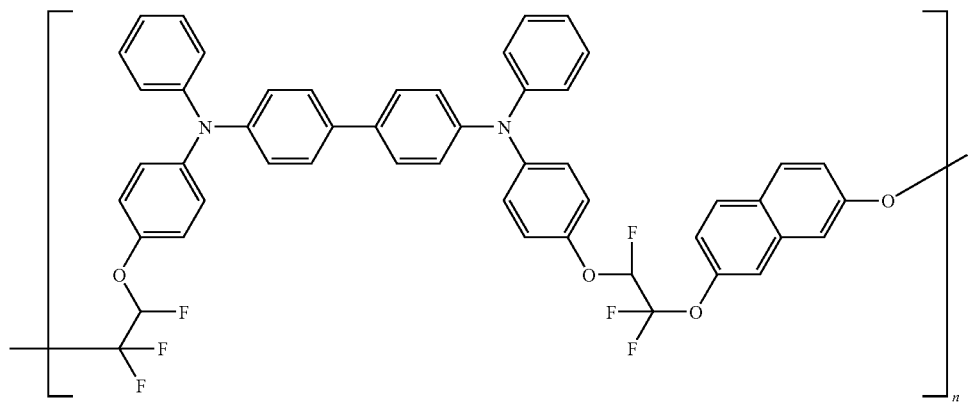

25)

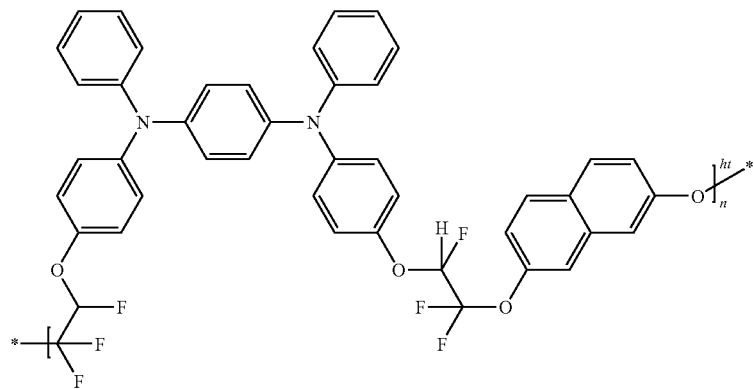

26)

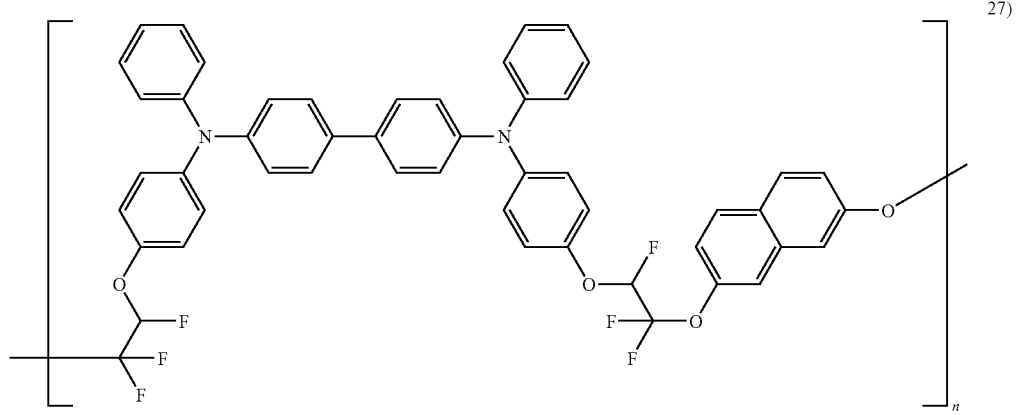
27)
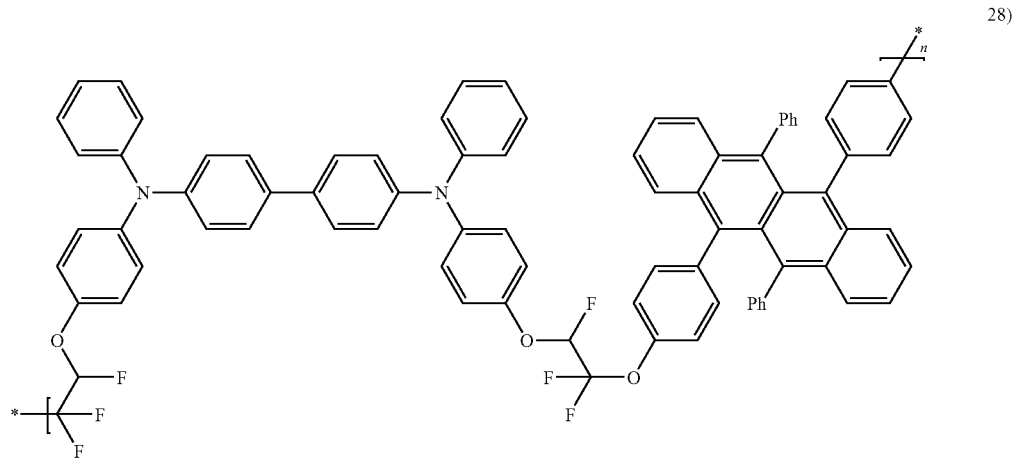
28)
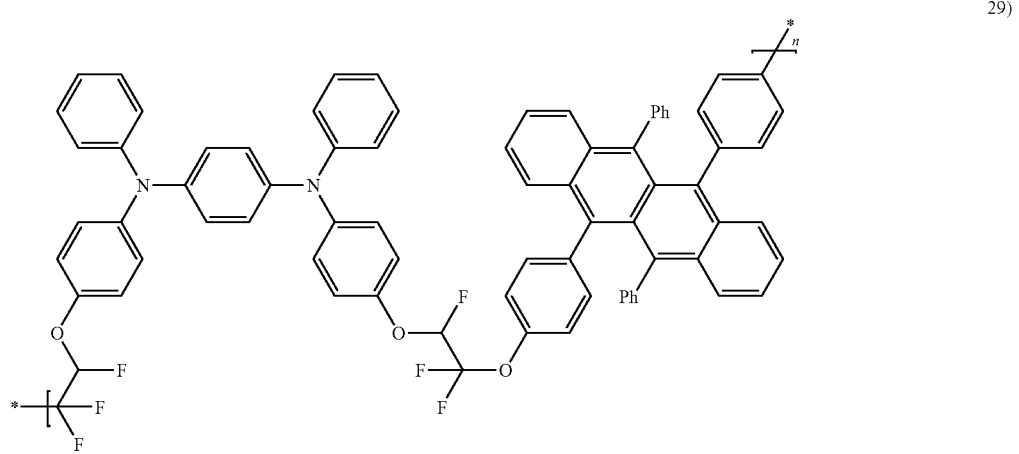
29)

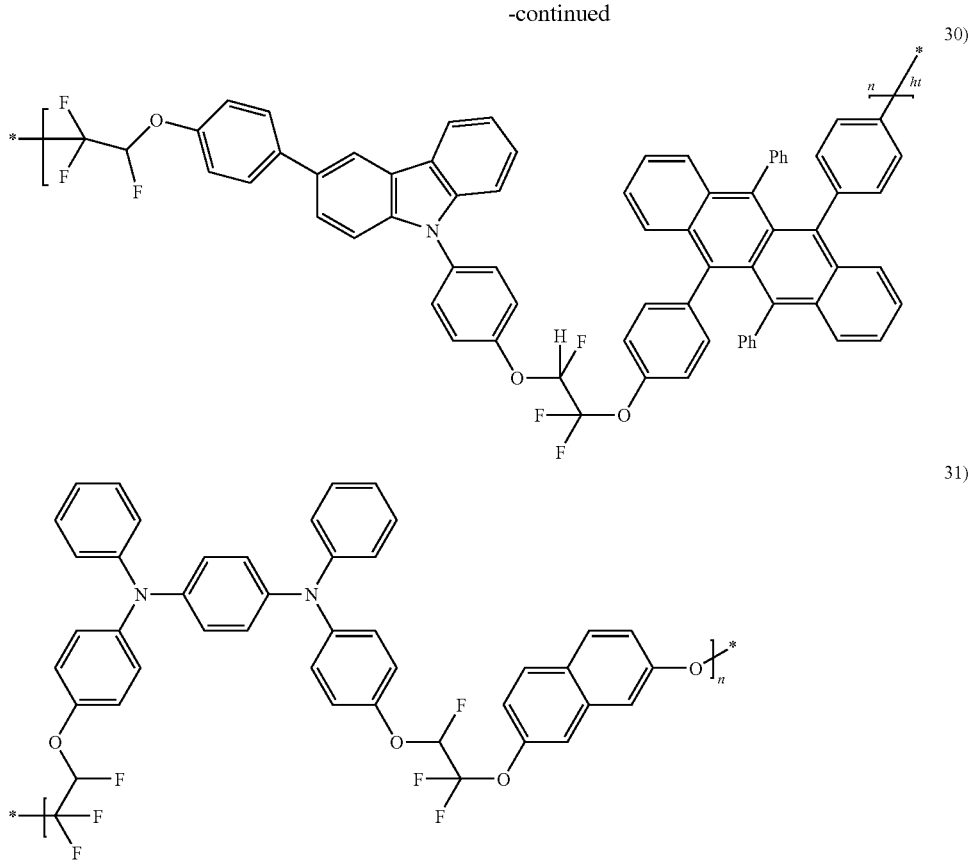

30)

31)

Molecular weight is not particularly limited, but the resulting polymers can have, for example, a number average molecular weight from, for example, about 1,000 g/mol to about 100,000 g/mol, or from about 5,000 g/mol to about 50,000 g/mol, or from about 10,000 g/mol to about 20,000 g/mol.

Polydispersity is not particularly limited, but the resulting polymers can have, for example, a PDI of 1-5 or from 1-2.

Polymers can be prepared such that crosslinking agents can be combined with the monomer or polymer to impart resultant films with properties necessary to support solution processing on top of the material. In one embodiment, for example, pendant alkylenoxy, alkene, or benzocyclobutane groups could be utilized during annealing to impart a crosslinked structure with sufficient insolubility for subsequent processing. Additionally, a material or component could be added to the polymer in the ink to provide for a crosslinked or entangled film structure that would also impart film with sufficient insolubility for subsequent processing on top of the film. See, for example, Thompson et al., *Chem. Mat.*, 2007, 19, 4827-4832; Meerholtz et al., *App. Phys. Lett.*, 2007, 91, 103507; Marks et al., *App. Phys. Lett.*, 2003, 82, 331-333; and Towns et al., WO 2006/043087.

Additional Embodiments

Monomers, oligomers, and polymers can also be prepared as follows:

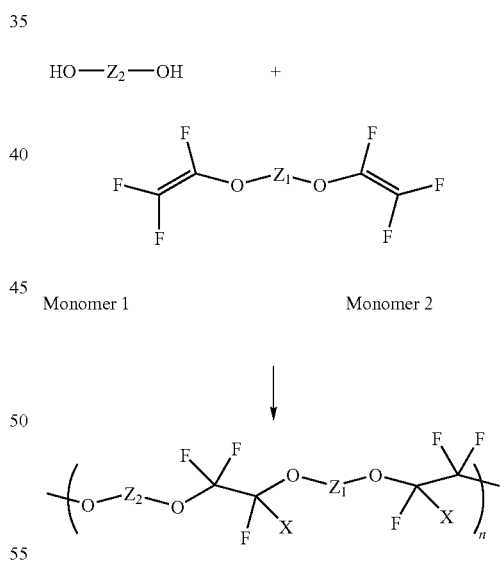

wherein X is H or F, for example, depending on polymerization conditions, and $Z_1$ and $Z_2$ are independently selected from a hole transport linkages and spacer linkages, provided at least one of $Z_1$ and $Z_2$ is a hole transport linkage, and the spacer linkage being selected from aromatics such as, for example, phenyl, naphthyl, and the like, alkylene, polyether, perfluoropolyether and perfluoroalkoxy. The spacer linkage does not need to provide hole transport or extended conjugation.

The presence of an alcohol either through, for example, in situ generation via de-protonation of the phenolic monomer using an alkoxide or the external addition of alcohol in cases, where a phenoxide is synthesized first and used in the reaction can lead to polymers with X being H. Alternatively, for example, when a reaction is carried out starting with a phenoxide, a fluoro cation source such as N-fluorobenzenesulfonamide can be added to obtain polymers with X being F.

Additionally, it may be desirable to have polymers, wherein the polymers are endcapped so as to eliminate chain termini with a fluorine or hydroxyl group as these may lead to operational instability. Polymers may be treated following synthesis to remove remaining fluorine substituents with phenol or an alkoxide. Terminal hydroxyl groups may also be blocked by alkylation with activated arenes or alkyl alkylating agents such as methyliodide. Also, polymers can be end-capped in situ during polymerization using a monofunctional material as known in polymer chemistry. The polymer could also be end-capped with cross-linkable functionalities such as a trifluorovinyloxy, vinylenic, acetylenic, oxetane, trichlorosilyl, trialkoxysilyl, epoxy to enhance intractability of layers. Incorporation of above groups can be accomplished either in situ during polymerization using monofunctional monomers with appropriate functional groups as described above or by a post-polymerization procedure. Representative and non-limiting examples of end-capping agents are shown below,

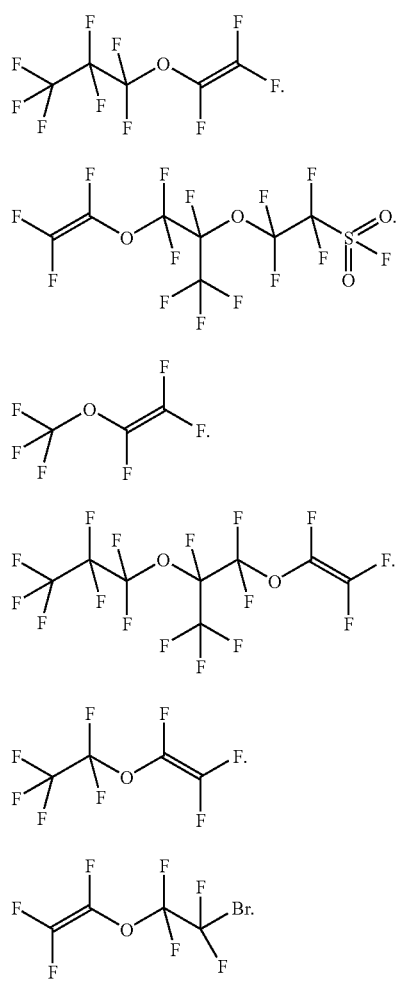

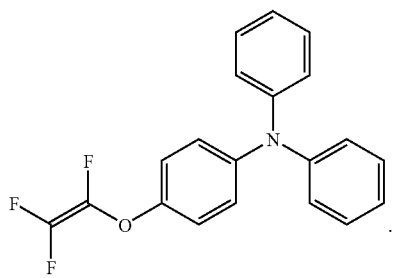

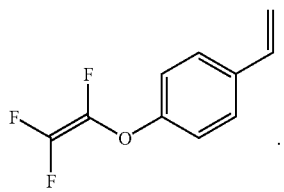

Polymer Properties

The polymers and copolymers can be soluble. They can be soluble in organic solvents.

Polymers of the present embodiments can advantageously serve as materials for hole injection layers, hole transport layers, a photoactive layers and electron blocking layers. For example, these polymers are stable and relatively resistant to hole transport degradation which can be brought on when excited states are generated in the polymer. Thus such polymers may offer added operational stability to various devices. These polymers can also increase the dielectric constant at an interface where the polymer is applied as a layer, thereby facilitating charge injection. Typically, this is understood within the context of band bending types of arguments. Here a properly oriented dipole at an interface can provide a sufficient internal field to allow for Fermi-level pinning between layers and thus, charge injection, despite a vacuum level misalignment. Moreover, these polymers exhibit orthogonal solvent compatibility for solution processed layers, which is highly useful for device layer formation. Without wishing to be limited to any particular theory, it is believed that the fluorinated chains contribute to orthogonal solvent compatibility of the polymers.

Additionally, it is desired that a polymer is selected to provide suitable HOMO-LUMO energetic properties such as to minimize deleterious impact on device operation.

Ink Compositions and Formulations

Polymers and co-polymers described herein can be combined with solvents, other polymers (as blends), additives, dopants or a combination thereof to form compositions such as inks that can be cast as a layer in various devices.

The polymers can be combined with at least one solvent to form an ink composition. For example, in one embodiment, a composition comprises a co-polymer comprising repeat units represented by:

wherein, $Ar^1$ is an arylamine, $Ar^2$ is an aryl, and $R^1$ and $R^2$ are independently selected from $C_1$-$C_{10}$ fluorinated alkyls; and at least one solvent.

Various solvents can be used. As a non-limiting example, the composition can comprise one of more of the following solvents: chlorobenzene, chloroform, 1,2-dichloroethane, 1,2-dichlorobenzene, 1,3-dichlorobenzene, 1,4-dichlorobenzene, trichlorobenzene, 1,3,5-trichlorobenzene, dichloromethane, ethylbenzoate, methylbenzoate, propylacetate, ethylacetate, butylacetate, phenylacetate, cyclohexanone, methyl iso-butyl ketone, pentanone, cyclohexane, methylethylketone, N,N-dimethylformamide, N,N-dimethylacetamide, N-methylpyrrolidinone, pyridine, piperidine, N-methylpyrrole, acetonitrile, benzonitrile, tetrahydrofuran, dioxane, 2-methyltetrahydrofuran, toluene, benzene, xylenes, mesitylene and 1,3-trifluoromethylbenzene, Ethylene glycol diethers, diethylene glycol diethers propylene glycol diethers, dipropylene glycol diethers, ethylene glycol monoether acetate, diethylene glycol monoether acetate, propylene glycol monoether acetate, dipropylene glycol monoether acetate, anisole, ethoxy benzene, dimethoxy benzenes. Additionally, the ink composition may comprise one or more solvents.

In one embodiment, the ink is substantially free from or totally free from protic solvents. For example, the amount of protic solvent can be less than 1 wt. %, or less than 0.1 wt. %.

Solvents are to be selected to provide an ink that yields a film of desired physical properties and performance with easily controllable thickness, composition and quality to provide an ink with a utility in a device that meets application needs. As a non-limiting example, the solvents may be selected from the lists found in the following references: Cheremisinoff, N. P. In *Industrial Solvents Handbook Second Edition*; Marcel Dekker: New York, N.Y., 2003; Ash, M.; Ash, In *Handbook of Solvents*; Synapse Information Resources Inc; 2$^{nd}$ Edition, 2003; Wypych, G. In *Handbook of Solvents (Chemical)*; Noyes Publications, 1$^{st}$ Edition, 2000; Hansen, C. M.; Durkee, J.; Kontogeorgis, G. In *Hanson Solubility Parameters: A User's Handbook*; Taylor and Francis, Inc, 2007 and hereby incorporated by reference in their entirety.

Ink solvent systems using two or more solvents, are described in U.S. 61/090,464 (filed on Aug. 20, 2008) and also U.S. application Ser. No. 12/541,500 filed Aug. 14, 2009, hereby incorporated by reference in their entirety.

The amount of solvent in an ink formulation can be between about 10% wt and about 99% wt, such as between about 90% wt and about 99% wt.

Alternatively, the weight percent of the co-polymers in an ink composition can be between about 0.01% wt and about 10% wt, such as between about 0.1% wt and about 1.0% wt.

The ink composition can further comprise at least one n-type polymer.

The ink composition can further comprise at least one p-type polymer.

The ink composition can further comprise at least one conjugated polymer.

In a particular formulation, the polymers of the present embodiments (used as p-type polymers) are combined with n-type polymers. The n- and p-type materials can be mixed in a ratio of for example from about 0.1 to 4.0 (p-type) to about 1 (n-type) based on a weight, or from about 1.1 to about 3.0 (p-type) to about 1 (n-type) or from about 1.1 to about 1.5 (p-type) to about 1 (n-type). The amount of each type of material or the ratio between the two types of components can be varied for the particular application.

Dopants

The present compositions optionally comprise one or more dopants.

Dopants are typically used to obtain a desired conductive state for a polymer component of an HIL or HTL and often result in improved device performance. For example, upon oxidation of a semi-conductive polymer by a redox dopant, electrons are removed from the valence band of the polymer. This change in oxidation state results in the formation of new energy states for the polymer. The energy levels are accessible to some of the remaining electrons in the valence band, allowing the polymer to function as a conductor/semi-conductor.

In the present compositions, in particular, the conductive conjugated polymer can be doped with a redox dopant. Examples of suitable redox dopants that are known in the art include, but are not limited to, quinones, boranes, carbocations, bora-tetraazapentalenes, aminium or ammonilium salts, sulfonium salts, oxonium salts, selenonoium salts, nitrosonium salts, arsonium salts, phosphonium salts, iodonium salts, select metal (e.g. silver) salts, or combinations thereof. Suitable redox dopants include, but are not limited to, those disclosed in U.S. Pat. Nos. 5,853,906 and 5,968,674, which are hereby incorporated by reference in their entireties.

The redox dopant can also be selected to provide a suitable charge balancing counter-anion. The type of dopant anion can affect the doping level of the conductive polymer and the device performance for devices prepared from these solutions.

The size and nature of the dopant anion can be an important parameter for modulating the efficiency of a device.

The anion/counterion can be a sulfonate anion, a chloride anion, a bromide anion, an iodide anion, an optionally substituted arylsulfonate anion, an optionally substituted alkylsulfonate anion, a perfluoroalkylsulfonate anion, or a material represented by formula (i) below:

$$[MY_p(ArX_n)_{4-p}]^-  \qquad (i)$$

where M=B or Ga; Ar is chosen independently from phenyl, naphthyl, anthracenyl, phenanthryl, thienyl, pyrrolyl, furyl, pyridyl, imidazolyl, benzimidazolyl; and X and Y can be independently selected from a halide (F, Cl, Br and I), cyanide, nitro, another optionally substituted aryl; p≦4; n≦10; or a material represented by formulat (ii) below:

$$[MY_p(ArX_n)_{6-p}]^-  \qquad (ii)$$

where M=P or Sb; Ar is chosen independently from phenyl, naphthyl, anthracenyl, phenanthryl, thienyl, pyrrolyl, furyl, pyridyl, imidazolyl, benzimidazolyl; and X and Y can be independently selected from a halide (F, Cl, Br and I), cyanide, nitro, another optionally substituted aryl; p≦4; n≦10.

In the final compositions, the composition can be distinctly different from the combination of original components (i.e., semi-conductive polymer and/or redox dopant may or may not be present in the final composition in the same form before mixing). Thus, the semi-conductive conjugated polymer and the dopant, or redox dopant, can refer to components that will react to form a doped conjugated polymer. In addition, some embodiments allow for removal of reaction byproducts from the doping process. For example, the iodonium redox dopant can result in organic byproducts that can be washed away from the doped polymer.

In some embodiments, the redox dopant is a photoacid. Examples of suitable photoacids include, but are not limited to, onium salts such as sulfonium and iodonium salts, for example, as described in *Journal of Polymer Science Part A, Polymer Chem.* 37, 4241-4254, 1999, hereby incorporated by reference in its entirety.

Iodonium salts are known in the art. Doping of a conductive polymer, such as a neutral polyarylamine, can be achieved using photoacids such as iodonium salts or diaryl iodonium salts, and in particular, diphenyl iodonium salts. The aryl groups such as a phenyl group in the iodonium salt can be optionally substituted as known in the art. For example, the redox dopant may be a lipophilic iodonium salt. Typically, the iodonium salt is represented by:

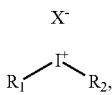

wherein independently $R_1$ is an optionally substituted aryl group, independently $R_2$ is an optionally substituted aryl group, and $X^-$ is an anion.

Doping of a neutral polyarylamine can also be achieved using a photoacid such as a sulfonium salt. Sulfonium salts are known in the art. The aryl groups in the sulfonium salt can be optionally substituted as known in the art. Typically, the sulfonium salt is represented by:

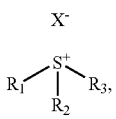

wherein independently $R_1$ is an optionally substituted arene, independently $R_2$ is a optionally substituted arene, $R_3$ is a optionally substituted arene, and $X^-$ is an anion.

The dopant can comprise an optionally substituted diphenyl iodonium salt with a molecular weight of, for example, about 100 g/mol to about 500 g/mol, or approximately 300 g/mol.

In some embodiments, the dopant is the photoacid 4-isopropyl-4'-methyldiphenyliodonium tetrakis(pentafluorophenylborate) (IMDPIB(PhF$_5$)$_4$), represented by:

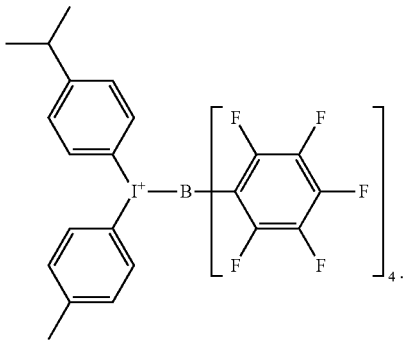

Examples of other iodonium salts that may be used, include, but are not limited to, diphenyliodonium hexafluorophosphate (DPIPF$_6$), diphenyliodonium para-toluene sulfonate (DPITos), bis-(4-tert-butylphenyl)iodonium trifluoromethane sulfonate ($^t$BDPITFSO$_3$), and diphenyliodonium perfluoro-1-butane sulfonate (DPIPFBSO$_3$). The iodonium salt can be a low molecular weight compound or it can be coupled to a high molecular compound such as a polymer.

The redox dopant may be a sulphonium salt. Examples of suitable sulphonium salts include, but are not limited to, triphenylsulphonium hexafluorophosphate, triphenylsulphonium para-toluene sulfonate, bis-(4-tert-butylphenyl)sulphonium trifluoromethane sulfonate, and diphenylsulphonium perfluoro-1-butane sulfonate.

Other onium salts may be used provided such that effective doping can be achieved for select counterions.

Another class of dopants that can be used includes quinones. Examples of suitable quinones that may be used to effect doping include, but are not limited to, tetrafluorotetracyano-p-quinodimethane (F$_4$TCNQ), trifluorotetracyano-p-quinodimethane (F$_3$TCNQ), difluorotetracyano-p-quinodimethane (F$_2$TCNQ), fluorotetracyano-p-quinodimethane (FTCNQ), dichloro dicyanoquinine (DDQ), o-chloranil and cyanil.

Further examples of suitable dopants include quinonediimine derivatives, including, e.g., those disclosed in U.S. Pat. No. 6,908,783 by Kuehl et al., which is incorporated by reference herein in its entirety.

Another class of dopants that can be used includes ammonium salts. Ammonium radical cations can be used as a redox additive to the formulation to undergo electron transfer. The byproducts formed need not necessarily be removed from the composition, as they are also hole transporting moieties and are less likely to adversely affect transport. Examples of suitable ammonium salts include, but are not limited to, tris-(4-bromophenyl)amine antimony hexachloride.

Other useful redox dopants include bora-tetraazapentalenes. Examples of a bora-tetraazapentalene are represented by:

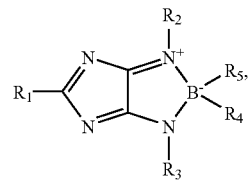

wherein $R_1$, $R_2$, $R_3$ are independently hydrogen, an optionally substituted or unsubstituted alkyl, a heteroalkyl, an aryl, a heteroaryl, a fused carbocycle or a fused heterocycle group, and wherein independently $R_4$ and $R_5$ are fluorine, hydrogen, an optionally substituted or unsubstituted alkyl, a heteroalkyl, an aryl, a heteroaryl, a fused carbocycle or fused heterocycle, or, together with the boron atom, a boron-containing heterocycle. (Rothe, Carsten, Laser and Photonics Reviews (2007), 1(4), 303-306; WO 2007115540 A1 20071018 and references therein.)

Another class of useful dopants is a silver salt, such as silver tetrafluoroborate, silver tetraphenylborate, silver hexafluorophosphate. Silver ions may undergo electron transfer to or from silver metal and the conductive polymer salt; U.S. Pat. Nos. 5,853,906 and 5,968,674.

In preparing the present compositions, the dopant is typically formulated first with the semiconductive polymer, to ensure that doping of the polymer occurs.

For example, in some embodiments, the composition is an ink formulation that is prepared by combining the conjugated polymer with the dopant to form a semiconductive polymer-dopant mixture. Typically, a stock solution of the semiconductive conjugated polymer (e.g., one made by dissolving or dispersing the semiconductive polymer in an organic solvent) is combined with a stock solution of the dopant, to form a polymer-dopant solution. Alternatively, in some embodiments, the dopant is covalently attached to the conductive conjugated polymer. In these embodiments, the compositions are prepared by combining the conductive polymer-dopant with the semiconducting matrix component to form the composition.

Amounts

The present compositions can comprise between about 1% and 99% by weight ("wt %," or "% (w/w)") of the semiconductive conjugated polymer, and, if a dopant is present, between about 0% and 75% by weight dopant. Weight percentages for each component are calculated on the basis of the weight of all solids in the composition.

For example, in some embodiments, the compositions comprise about 10% to about 90%, about 15% to about 80%, about 25% to about 75%, about 30% to about 70%, or about 35% to about 65% by weight of the semiconductive conjugated polymer with respect to the total amount of semiconductive polymer, and dopant, if present.

In addition, the dopant can be present in an amount that corresponds to the molar amount of repeat units of the semiconductive conjugated polymer. For example, the dopant is typically present in the composition in an amount of about 0.01 moles dopant/moles semiconductive polymer repeat unit ("m/ru") to about 1 m/ru, wherein m is the molar amount of dopant and ru is the molar amount of semiconductive polymer repeat units. In some embodiments, the dopant is present in an amount of about 0.01 m/ru to about 0.5 m/ru, about 0.1 m/ru to about 0.4 m/ru, or about 0.2 m/ru to about 0.3 m/ru. Typically, the dopant is present in an amount of about 0.2-0.3 m/ru. In some embodiments, a dopant is not present in the composition.

Devices and Applications

Polymers and compositions formed using the polymers can be used to create device layers in various devices. Thus in one embodiment, a device comprises a layer comprising a co-polymer comprising repeat units represented by

  (I)

  (II)

wherein, $Ar^1$ is an arylamine, $Ar^2$ comprises an aryl, and $R^1$ and $R^2$ are independently selected from $C_1$-$C_{10}$ fluorinated alkyleneoxy.

The device can be, but is not limited to, OLED, PLED, PHOLED or OPV devices.

The polymers can be used, for example, to form a hole injection layer. The polymers can be used to form a hole transport layer. The polymers can be used to form a photoactive layer. The polymers can be used to form an electron blocking layer.

Devices can be made according known methods in the art using the polymers of the present embodiments. The compositions, including inks, can be deposited as hole injection layers, hole transporting layers, electron blocking layers, and active layers in various devices.

The polymer compositions can be, for example, deposited by spin casting, ink jetting, doctor blading, spray casting, dip coating, vapor depositing, or any other known deposition method, on top of the HIL film. The deposited film can be then, for example, optionally annealed at about 40 to about 250° C., or from about 150 to 180° C., for about one minutes to two hours, such as 10 min to an hour, in, for example, an inert atmosphere.

The thickness of the layers cast with the polymer compositions can be, for example, from about 10 nm to about 300 nm thick, or from 30 nm to 60 nm, 60 nm to 100 nm, or 100 nm to 200 nm. The film then can be optionally dried/annealed at 110 to 200° C. for 1 min to an hour, optionally in an inert atmosphere. Methods for annealing are known in the art. Solvent annealing can be also carried out.

Examples of organic electronic devices that can be fabricated from the present compositions include, but are not limited to, OLEDs, PLEDs, PHOLEDs, SMOLEDs, ESDs, photovoltaic cells, as well as supercapacitors, hybrid capacitors, cation transducers, drug release devices, electrochromics, sensors, FETs, actuators, and membranes. Another application is as an electrode modifier including an electrode modifier for an organic field effect transistor (OFETS). Other applications include those in the field of printed electronics, printed electronics devices, and roll-to-roll production processes. Additionally, the compositions discussed herein may be a coating on an electrode.

The present compositions can be used to form HTLs for organic photovoltaic devices (OPVs). Organic photovoltaics are generally described in, for example, *Organic Photovoltaics*, S-S, Sun, N. Sariciftci, 2005. OPVs are known in the art. See, for example, US Patent Publ. No. 2006/0076050, published Apr. 13, 2006; see also WO 2008/018931, published Feb. 14, 2008, including descriptions of OPV active layers. See also U.S. provisional Appl. No. 61/043,654, filed Apr. 9, 2008, by Williams et al., entitled "Hole Collection Layer Compositions and Photovoltaic Devices," which is herein incorporated by reference in its entirety. The devices can comprise, for example, multi-layer structures that include, for example, an anode, including a transparent conductor such as indium tin oxide (ITO) on glass or PET; a hole injection layer and/or a hole transport layer; a P/N bulk heterojunction layer; a conditioning layer such as LiF; and a cathode such as for example Ca, Al, or Ba. For example, a variety of photoactive layers can be used in OPV devices. Photovoltaic devices can be prepared with photoactive layers comprising fullerene derivatives mixed with, for example, conducting polymers as described in for example U.S. Pat. Nos. 5,454,880 (Univ. Cal.); 6,812,399; and 6,933,436. Also, photoactive layers may comprise blends of conducting polymers, blends of conducting polymers and semiconducting nanoparticles, and bilayers of small molecules such as pthalocyanines, fullerenes, and porphyrins.

LEDs and OLEDs are generally described in, for example, *Organic Light-Emitting Materials and Devices* (Ed., Z. Li, H. Meng), 2007. See also, for example, EP 1950818 (Samsung SDI)

For example, the present compositions can be used to form HILs for OLED devices. OLED devices are known in the art. See, for example, US Patent Appl. Publ. No. US 2006/00787661 A1, published Apr. 13, 2006. See also Hammond et al., US Patent Appl. Publ. No. US 2006/0175582 A1, published Aug. 10, 2006, entitled "Hole Injection/Transport Layer Compositions and Devices." The devices can comprise, for example, multi-layer structures that include, for example, an anode, including a transparent conductor such as ITO on glass or PET or PEN; a hole injection layer; an electroluminescent layer such as a polymer layer; a conditioning layer such as LiF, and a cathode such as for example Ca, Al, or Ba. See also U.S. Pat. Nos. 4,356,429 and 4,539,507 (Kodak).

Materials for and methods of preparing each of these layers or components are well known in the art. For example, conjugated polymers which emit light, for use in electroluminescent layers in OLEDS, are described, for example, in U.S. Pat. Nos. 5,247,190 and 5,401,827 (Cambridge Display Technologies). See also Kraft et al., "Electroluminescent Conjugated Polymers—Seeing Polymers in a New Light," *Angew. Chem. Int. Ed.*, 1998, 37, 402-428, including device architecture, physical principles, solution processing, multilayering, blends, and materials synthesis and formulation, which is hereby incorporated by reference in its entirety. Light emitters known in the art and commercially available can be used, including various conducting polymers as well as organic molecules, such as materials available from Sumation, Lumtec, Merck Yellow, Merck Blue, American Dye Sources (ADS), Kodak (e.g, AlQ3 and the like), and even Aldrich such as BEHP-PPV. Such polymer and small-molecule materials are well known in the art and are described in, for example, U.S. Pat. No. 5,047,687 issued to VanSlyke; and Bredas, J.-L., Silbey, R., eds., Conjugated Polymers, Kluwer Academic Press, Dordrecht (1991). See also "Organic Light-Emitting Materials and Devices," Z. Li and H. Meng, Eds., Leo et al. Chemical Reviews, 107, 2007, 1233-1271, CRC Press (Taylor and Francis Group, LLC), Boca Raton (2007), in particular, chapter 1 (pp. 1-44), chapter 2 (pp. 45-294), chapter 3 (pp. 295-412), and chapter 10 (pp. 617-638), for a fuller description of OLED components and layers.

The fabricated devices can be tested for device performance using methods known in the art. For example, for OLEDs, methods known in the art can be used to measure such device performance parameters as brightness, efficiency, and lifetime.

Methods known in the art can be used to measure OLED performance parameters. Device performance measurements are typically carried out at 10 mA/cm$^2$. For example, the protocol outlined below can be used to measure OLED device performance parameters of current density (mA/cm$^2$), operating voltage (V), brightness (cd/m$^2$), and efficiency (cd/A).

Examples of typical OLED parameters are as follows:

Typical OLED device voltages can be, for example, from about 2 to about 15, or about 2 to about 8, or about 2 to 5, or from about 3 to about 14, or from about 3 to about 7. Typical device brightness can be, for example, at least 100 cd/m$^2$, or at least 500 cd/m$^2$, or at least 750 cd/m$^2$, or at least 1,000 cd/m$^2$. Typical device efficiencies can be, for example, at least 0.25 cd/A, or at least 0.45 cd/A, or at least 0.60 cd/A, or at least 0.70 cd/A, or at least 1.00 cd/A, or at least 2.5 cd/A, at least 4.00 cd/A, or at least 5.00 cd/A. Typical device lifetimes can be measured at 50 mA/cm$^2$ or up to 75 mA/cm$^2$ in hours and can be, for example, at least 50 hours, or at least 100 hours, or at least about 900 hours, or at least 1,000 hours, or at least 1100 hours, or at least 2,000 hours, or at least 5,000 hours, or at least 10,000 h, or at least 20,000 h, or at least 50,000 h.

The present compositions, when used as HILs or HTLs in organic devices, typically lead to increases in device parameters such as power efficiency. For example, in some embodiments, the present compositions, when used as HILs in OLEDs, can lead to increases in efficiency of at least 5%, or at least about 10% or greater, up to about 50%, depending on the operating voltage and quantum efficiency of the OLED in the absence of a good hole injection layer, compared to OLEDs fabricated using traditional HILs that contain an insulating matrix component.

Other references teaching electronic devices and methods of making and using same include, for example: US Patent Publications 2006/0076050; 2006/0078761; 2006/0175581; 2006/0237695; 2007/0065590; 2008/0248313, assigned to Plextronics, Inc.

Working Examples

Various embodiments are described further with use of non-limiting working examples.

Example 1

Synthesis of poly(TPD-TFVBPA)

Synthesis of poly(TPD-TFVBPA) was carried out according to the following reaction scheme.

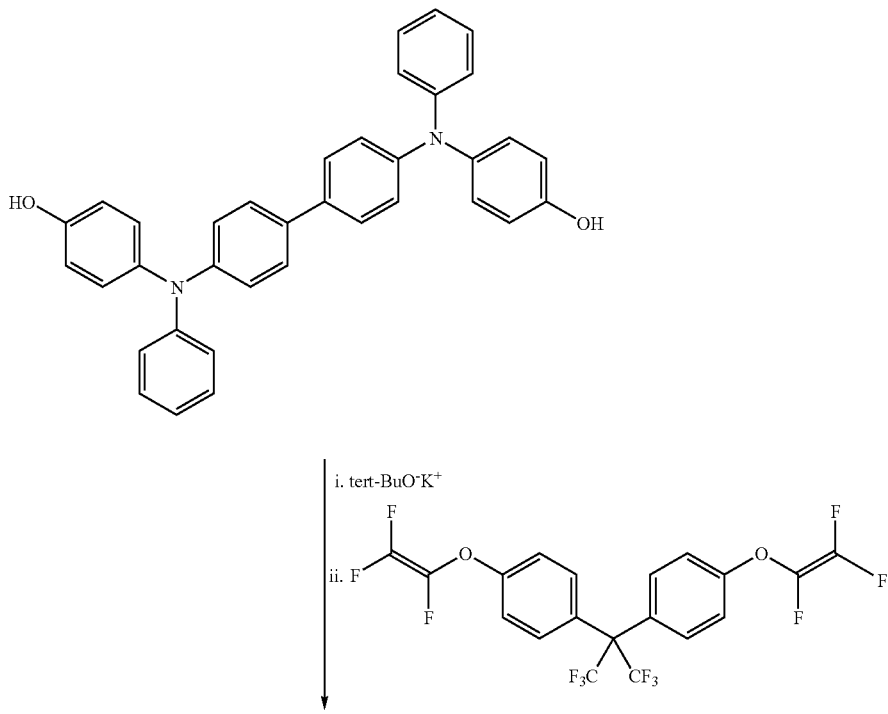

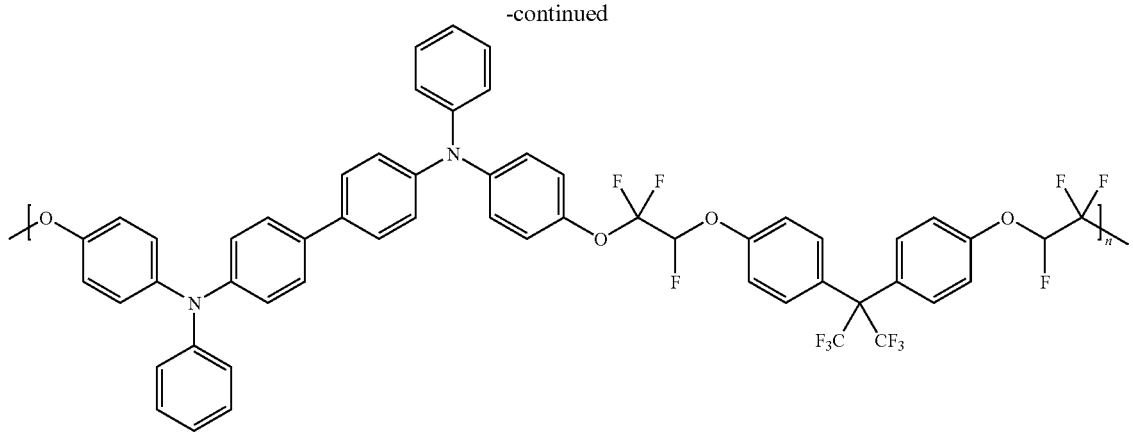

Figure 4:
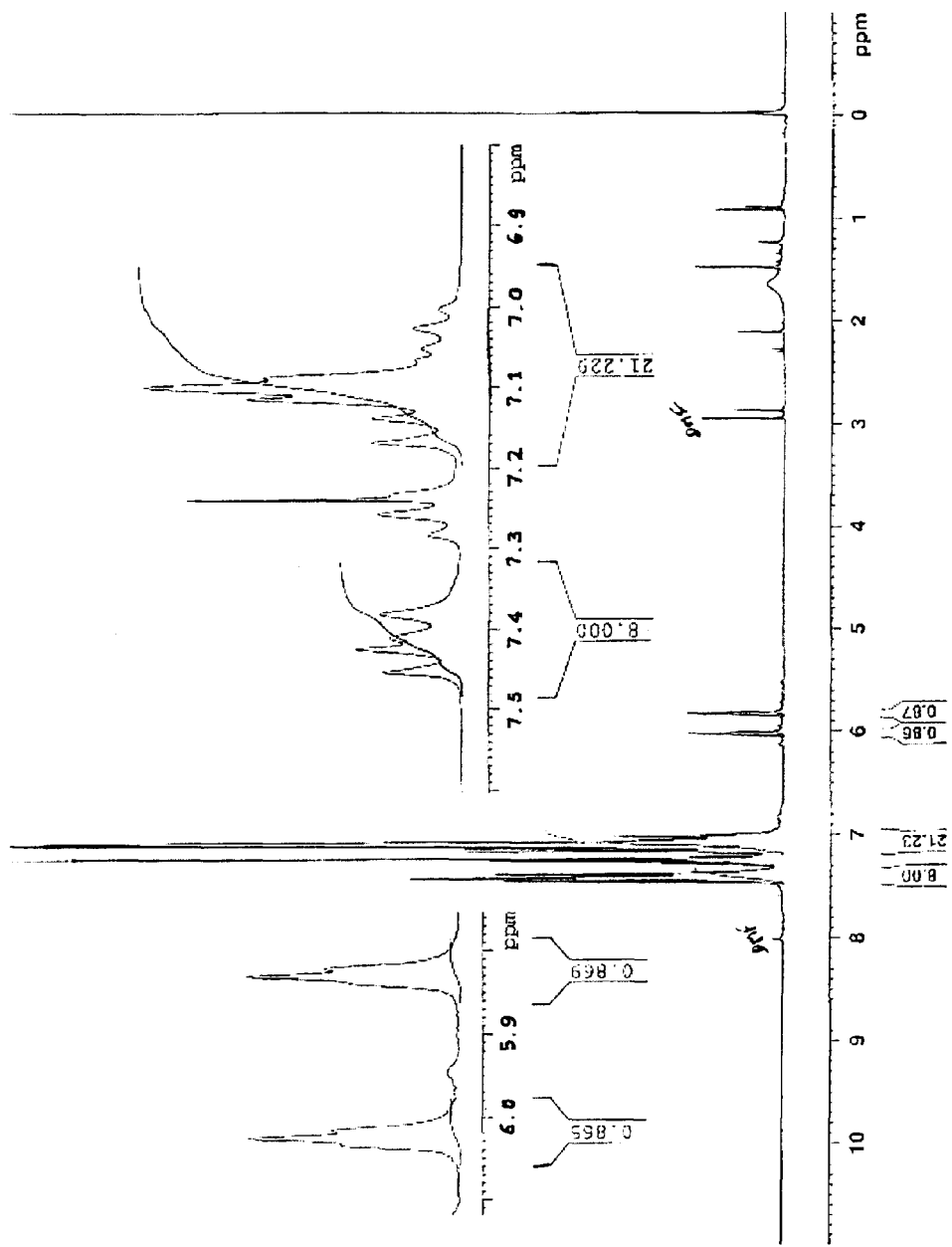
FIG. 4 shows $^1$H-NMR spectra of an embodiment for the copolymer.
Figure 5:
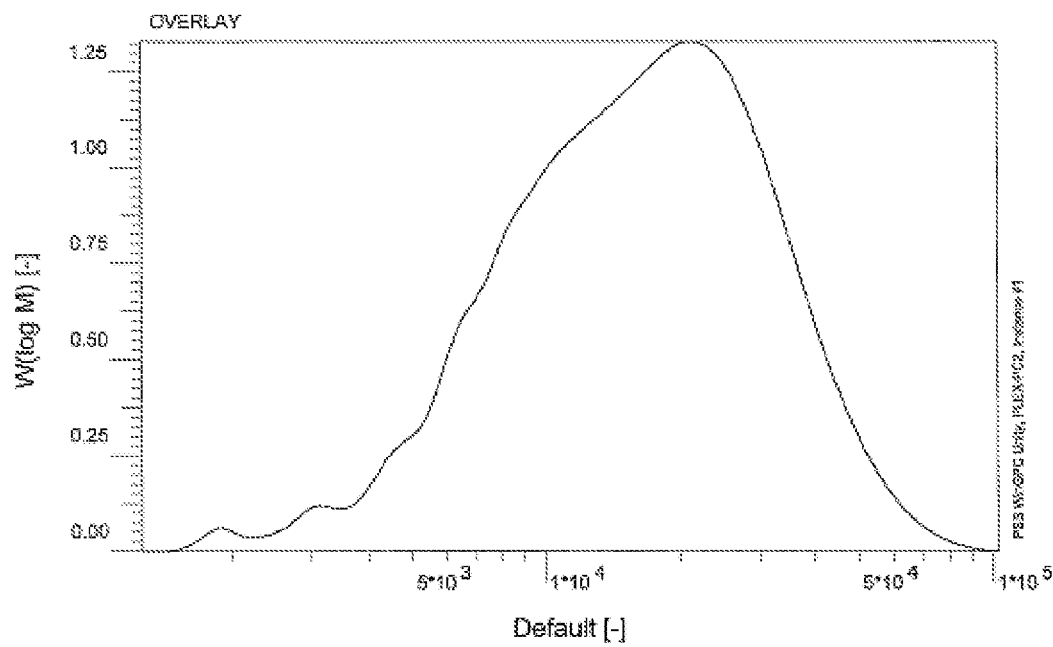
FIG. 5 shows gel permeation chromatographic analysis of an embodiment for the copolymer.
Figure 6:
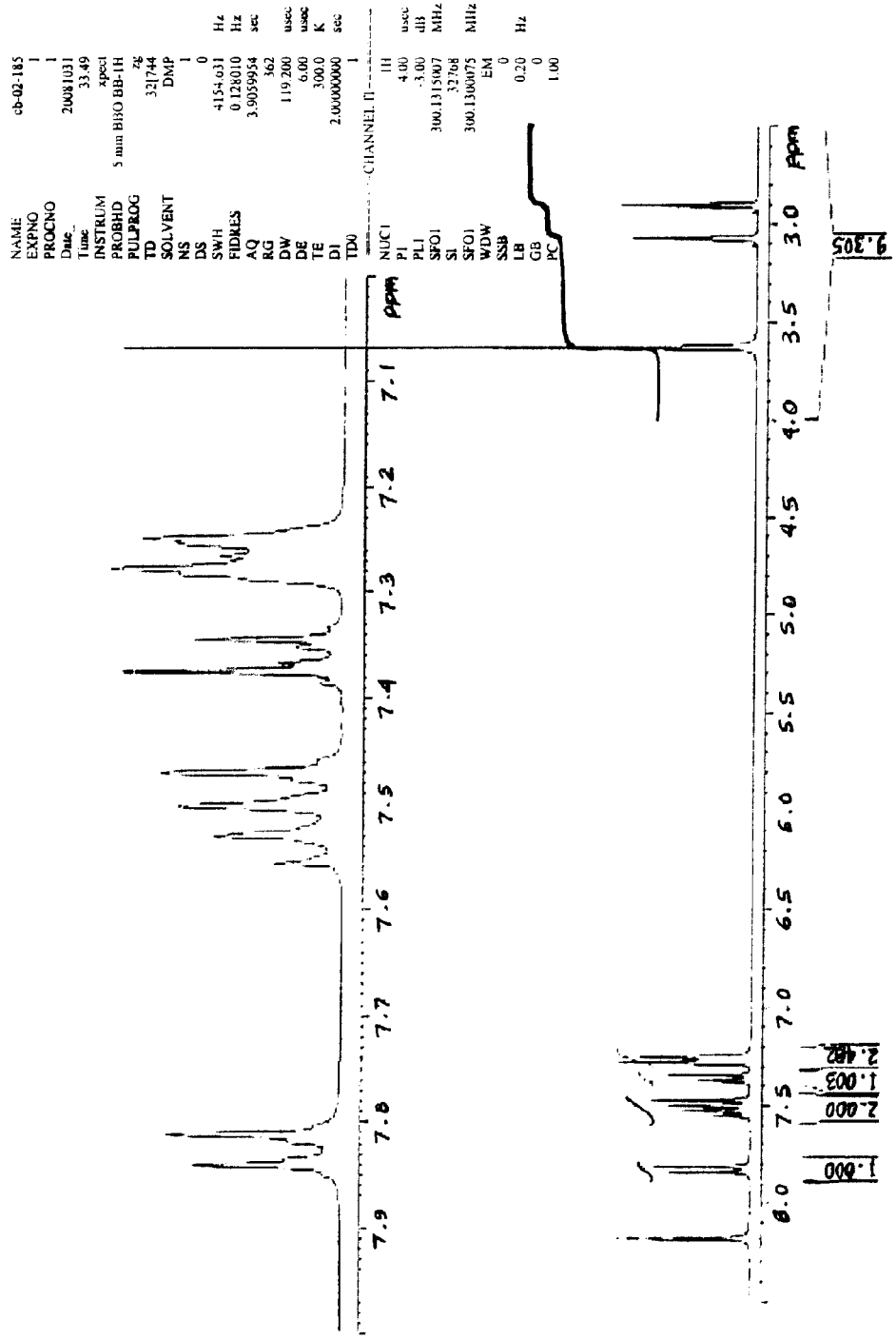
FIG. 6 Shows proton NMR of TPD-TFV monomer
Figure 7:
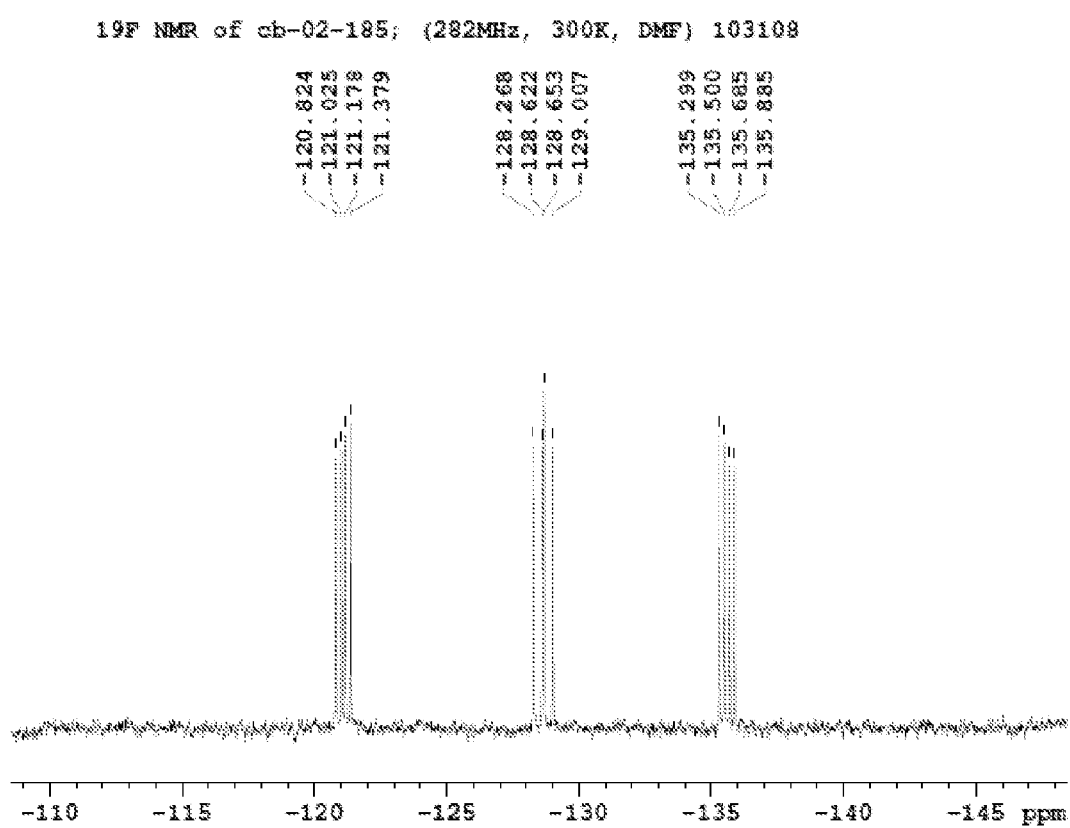
FIG. 7 Shows Fluorine NMR of TPD-TFV monomer

To a clean flame dried 100 mL 2 necked Schlenck flask added 0.911 gms of TPD-(OH)$_2$ which can be prepared in a manner similar to that found in *J. Mater. Chem.* (2008), 18(12), 1296-1301. 5 mL anhydrous N,N-dimethylformamide (DMF) was injected into the septa sealed flask and upon dissolution of the solids, 98 mg potassium tert-butoxide was added. The solution turned light yellow from orange-red. The contents were stirred at room temperature under nitrogen for 20 min and 0.886 g of 4,4'-(perfluoropropane-2,2-diyl)bis((1,2,2-trifluorovinyloxy)benzene) (Oakwood Products) dissolved in 5 mL anhydrous DMF was added via syringe. The vial which contained the trifluorovinylether monomer was rinsed once with 5 mL anhydrous DMF and the washings added to the reaction flask. The reaction was continued at room temperature for 17.5 hours at which time 0.05 ml of the polymer chain terminating agent, perfluoro(5-methyl-3,6-dioxanon-1-ene), obtained from Synquest Labs was added. The reaction was continued at room temperature for another 8 hrs and precipitated by pouring into 250 mL ethanol at room temperature. The precipitated polymer was centrifuged and dried in a vacuum oven after decanting supernatant. About 1.4 gms of dry solids were obtained, which was dissolved again in 15 mL anhydrous tetrahydrofuran and precipitated into 200 mL ethanol. The polymer was then centrifuged and the supernatant decanted. The white polymer was then placed on a 0.45 μm PVDF hydrophobic membrane filter and washed with ethanol (~50 mL). The polymer was finally dried in a vacuum oven at room temperature for 24 hours to obtain 0.88 gms of white powder. Structure was confirmed by Nuclear Magnetic Resonance spectroscopy (see FIG. 4), and Gel Permeation Chromatography (GPC) using chloroform as eluent and calibrated using poly(styrene standards) (see FIG. 5 indicating Mn=12,221 (PDI=1.59) for the polymer).

Example 2

Synthesis of TPD-TFV Monomer

Synthesis of TPD-TFV monomer was carried out according to the following reaction scheme.

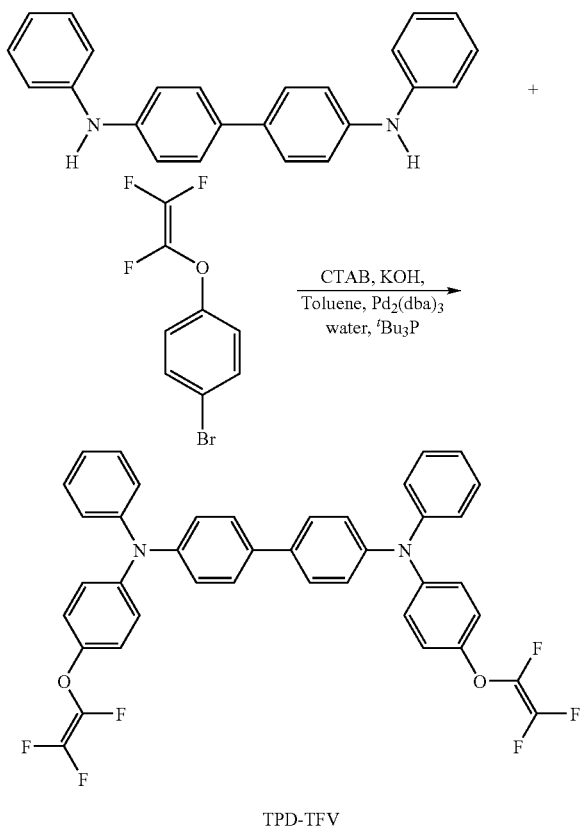

TPD-TFV

To a clean flame dried 500 mL 3 necked Schlenck flask with a thermometer and reflux condenser was added 10 gms of N,N'-diphenylbenzidine (Aldrich Chemicals), 10 gms of potassium hydroxide, 140 mg of hexadecyltrimethylammonium bromide, 250 ml of toluene, 16.7 gms of 1-bromo-4-(trifluorovinyloxy)benzene (Oakwood Chemical) and 5 ml of deionized water. This stirred mixture was degassed with bubbling nitrogen for 15 minutes. To this reaction mixture was added 14.7 ml of 0.33 M tri-tert-butylphosphine (Aldrich) in anhydrous oxygen free toluene. With vigorous stirring 1.36 gms of Pd$_2$ dba$_3$ was added all at once and reaction was sealed under a nitrogen blanket and heated to 98° C. for 14.5 hours. The reaction was cooled to room temperature and to this stirred solution (black-brown and homogeneous) was added ~5 g of MgSO₄. This was stirred until the MgSO₄ was free flowing (having absorbed all the water) and filtered through a medium glass frit and absorbed onto 100 grams of SiO₂. This was loaded onto a large silica-gel column with 90% hexanes: chloroform eluent. The column was eluted with same to remove non-polar byproducts. The polarity was then increased to 30% chloroform to elute the desired material to yield 14.98 g of a free flowing white solid for a 74% yield. Proton and fluorine NMR were consistent with the assigned structure.

Comparative Example 2A

Attempted Synthesis of TPD-TFV Monomer

To a clean flame dried 500 mL three necked round bottom flask 10.0 g of N,N' diphenyl benzidine followed by 200 mL of dry toluene was added. To this slurry 10.0 g of sodium tert-butoxide was added, and the reaction mixture was purged with nitrogen for 15 min. Then 17.8 g of p-bromo trifluorovinyloxybenzene and 1.15 g Pd2(dba)3 was added to the reaction flask. 8.5 mL of 2.30 M tert-Bu₃P in toluene then added to the reaction flask and heating was started. The reaction was refluxed overnight and all the solvent was stripped on a rotary evaporator. The reaction mixture was purified via column chromatography using methylene chloride-hexane mixtures to obtain 4.3 g of white solids. ¹H NMR indicated presence of tert-butyl groups on the compound and ¹⁹F NMR indicated possible undesired conversion of the trifluorovinyloxy functionality to some other fluorinated alkyl species. This suggested possible undesired nucleophilic substitution of tert-butoxide on the trifluorovinyloxy functionality.

Example 3

Synthesis of poly(nap-TPD-TFV)

Synthesis of poly(nap-TPD-TFV) was carried out according to the following reaction scheme.

Figure 8:
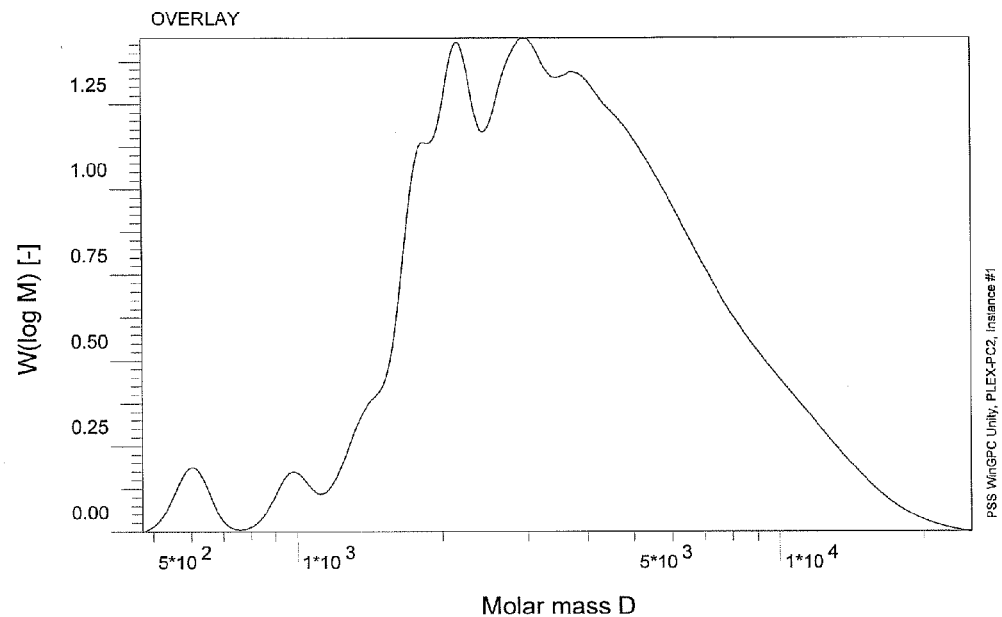
FIG. 8 Shows GPC for poly(nap-(TPD-TFV)
Figure 9:
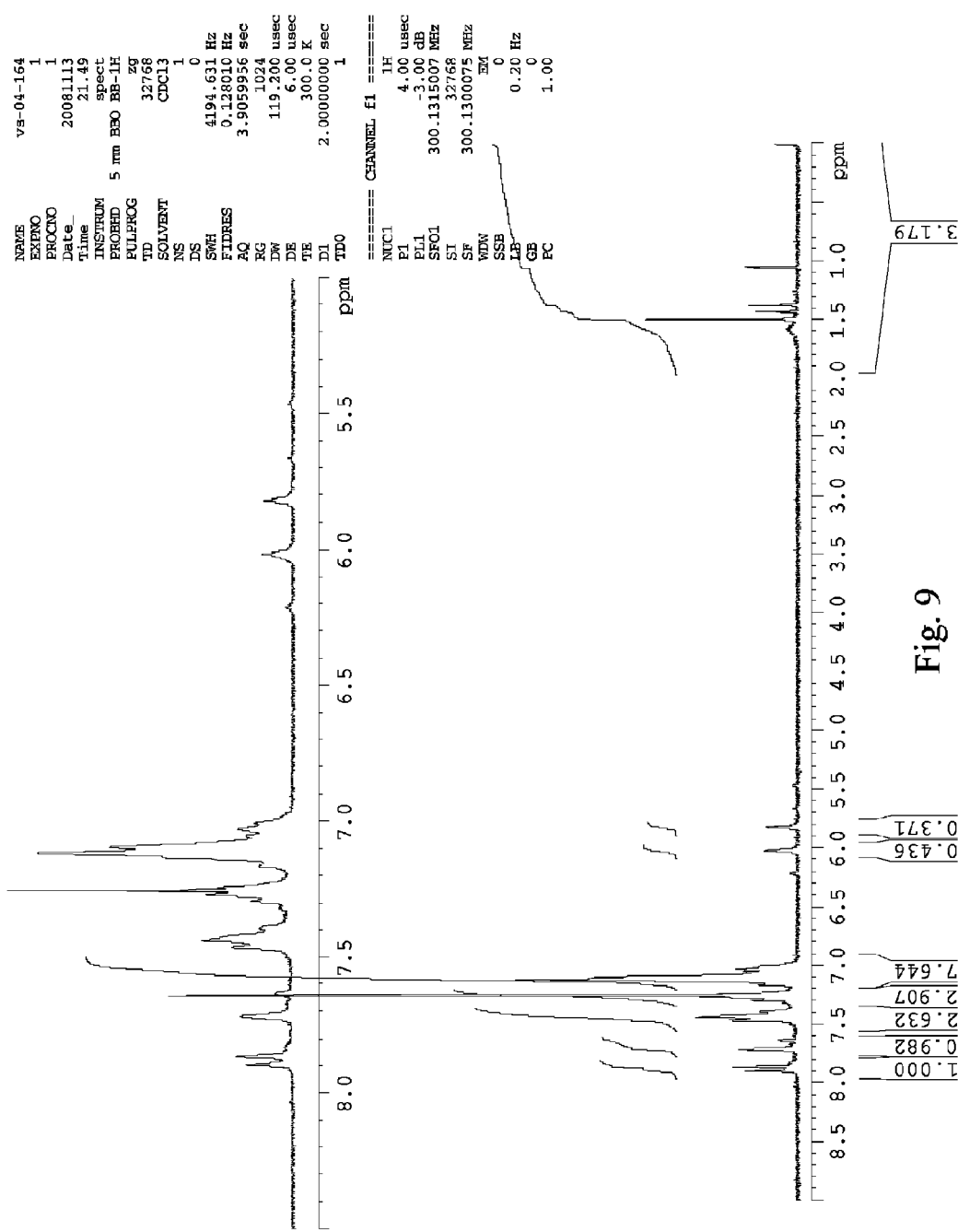
FIG. 9 Shows NMR for poly(nap-(TPD-TFV)

To a dry nitrogen flushed 100 mL two-neck RBF added 1.0 g 4,4'-bis(trifluorovinyloxy) tetraphenyl benzidine, 0.165 g potassium tert-butoxide (sublimed grade from Aldrich) and 0.235 g 2,7-dihydroxynaphthalene in a glove-box. The flask was sealed with rubber septa and 12 mL anhydrous DMF was injected into the flask. The reaction mixture was stirred at room temperature under nitrogen pressure overnight. The reaction mixture was then heated to 50° C. for 7 hrs and, subsequently, 0.2 mL perfluoro(5-methyl-3,6-dioxanon-1-ene) was injected and the reaction continued overnight at room temperature. The polymer was then precipitated into 100 mL methanol (semi-conductor grade, Aldrich) and centrifuged at 2000 rpm for 15 min. After discarding the supernatant, the centrifugate was shaken with 100 mL methanol (semi-conductor grade, Aldrich) and centrifuged again at 2000 rpm for 15 min. The white polymer was dried in a vacuum oven at room temperature after carefully pouring out the supernatant. The solids were then dissolved in 10 mL anhydrous THF (from Mbraun solvent delivery system), filtered through a 0.45 micron syringe filter and precipitated into 100 mL methanol (semi-conductor grade, Aldrich). The solvent was stripped on a rotary evaporator, and the polymer suspended in 20 mL methanol and filtered over a hydrophilic membrane filter (Millipore #SVLP09050) and dried in vacuo at room temperature to obtain 500 mg of white polymer. Gel Permeation Chromatography (GPC) using chloroform as eluent and calibrated using poly(styrene standards), see FIG. 8, Mn=2,893 (PDI=1.52).

The glass transition temperatures ("$T_g$"), melting points ("$T_m$"), and decomposition onset temperatures ("$T_{decomp,onset}$") were determined. The glass transition temperatures of the polymers were obtained using a TA Instruments (DSCQ200) Differential Scanning Calorimeter at a ramp rate of 20° C./min. Decomposition temperatures were obtained

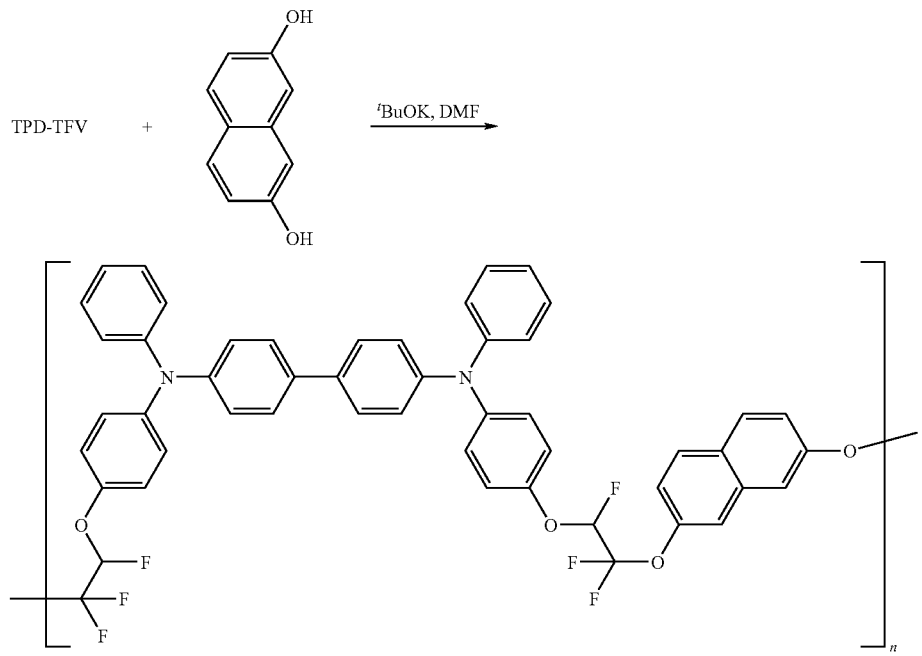

using a (TGAQ500) thermogravimetric analyzer at a ramp rate of 50° C./min. Tg (poly(nap-TPD-TFV)=100° C.

Example 4

Ink Compositions and HIL Study

A series of HIL ink compositions were prepared using Poly(TPD-TFVBPA) and IMDPIB(PhF$_5$)$_4$, as dopant. The compositions are shown in Table 1 below.

The ink composition were obtained using the following general procedure: separate stock solutions of Poly(TPD-TFVBPA) and IMDPIB(PhF$_5$)$_4$, in chlorobenzene or PMA were first prepared, each containing 1% (w/w) solids. Various amounts of each stock solution were then combined as indicated in Table 1.

TABLE 1

Compositions containing poly(TPD-TFVBPA) and 4-isopropyl-4'methyldiphenyliodonium tetrakis(pentafluorophenyl)borate

| HIL # | Poly(TPD-TFVBPA) (wt %) | IMDPIB(PhF$_5$)$_4$ (wt %) | Chlorobenzene (wt %) |
|---|---|---|---|
| 1 | 0.75 | 0.25 | 99 |
| 2 | 0.85 | 0.15 | 99 |
| 3 | 0.95 | 0.05 | 99 |

The resulting combined solution was refluxed for 2 h under a nitrogen blanket and stored in the glove-box.

Additionally, several ink formulations were made using (TPD-TFV—Example 2) and IMDPIB(PhF$_5$)$_4$, as dopant, in PMA Propylene glycol monomethyl ether acetate, as shown in Table 2.

TABLE 2

Compositions containing TPD-TFV and 4-isopropyl-4'methyldiphenyliodonium tetrakis(pentafluorophenyl)borate.

| HIL # | TPD-TFV (wt %) | IMDPIB(PhF$_5$)$_4$ (wt %) | PMA (wt %) |
|---|---|---|---|
| 4 | 0.7721 | 0.2279 | 99 |
| 5 | 0.6931 | 0.3069 | 99 |
| 6 | 0.6288 | 0.3712 | 99 |
| 7 | 0.7721 | 0.2279 | 99 |
| 8 | 0.6931 | 0.3069 | 99 |
| 9 | 0.6288 | 0.3712 | 99 |
| 10 | 1.634 | 0.366 | 98 |
| 11 | 1.381 | 0.619 | 98 |

Hole Injection Layer (HIL) Study

Ink compositions 1-9 from Tables 1 and 2 were spun on top of the ITO surfaces to prepare an HIL layer. A different HIL layer serving as a comparative benchmark ("Comparative HIL 1") was formed from an ink composition shown in Table 3 below:

TABLE 3

Composition of Comparative HIL 1

| Material | Wt. % |
|---|---|
| P3MEET-S* | 0.13 |
| Poly(4-vinylphenol) | 1.94 |
| Poly(styrenesulfonic acid) | 0.07 |
| Nafion | 0.07 |
| Water | 53.79 |
| Butyl Cellosolve | 44.01 |

*P3MEET-S is sulfonated poly(3-methoxyethoxyethoxythiophene) as described in US Patent Publication No. 2008/0248313 filed Jul. 13, 2007, assigned to Plextronics, Inc.

Figure 2:
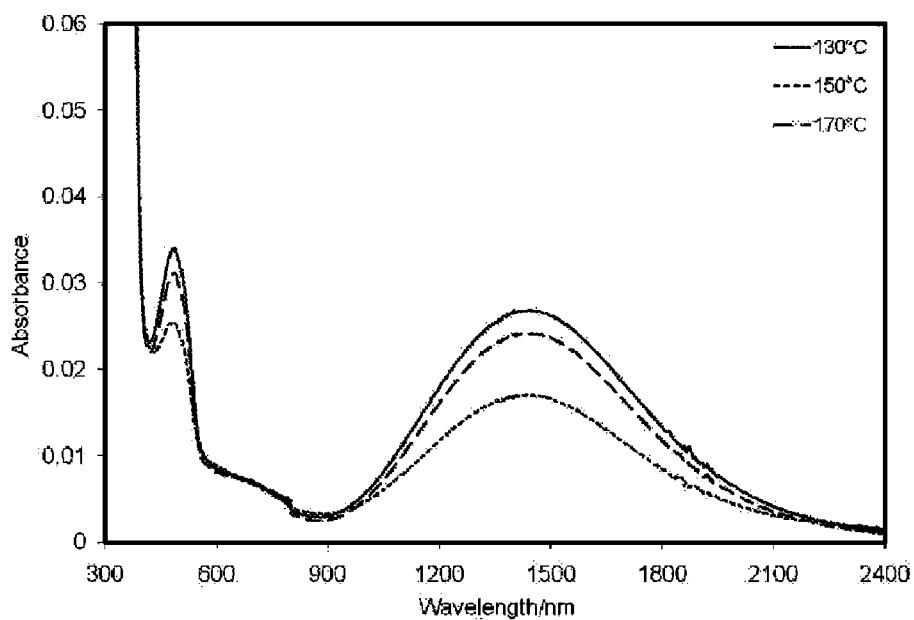
FIG. 2 is UV-vis-NIR spectra of thin films of poly(TPD-TFVBPA) doped with 4-isopropyl-4' methyldiphenyliodonium tetrakis(pentafluorophenyl)borate cast on a glass substrate from a solution in chlorobenzene and annealed at three temperatures.

Absorbance, fluorescence and UV-vis NIR spectra of thin films formed using poly(TPD-TFVBPA) ink compositions were obtained. FIG. 1 shows absorbance and fluorescence spectra of thin films of poly(TPD-TFVBPA) on a glass substrate. FIG. 2 shows UV-vis-NIR spectra of thin films of poly(TPD-TFVBPA) doped with 4-isopropyl-4' methyldiphenyliodonium tetrakis(pentafluorophenyl)borate cast on a glass substrate from a solution in chlorobenzene and annealed at three temperatures. A doping profile for oxidation of polymer was observed.

Example 5

Device Fabrication

OLED devices were fabricated following procedures known in the art. The devices were fabricated on indium tin oxide (ITO) surfaces deposited on glass substrates. The ITO surface was pre-patterned to define the pixel area of 0.05 cm$^2$. The device substrates were cleaned by ultrasonication in a dilute soap solution for 20 minutes followed by distilled water washes. This was followed by ultrasonication in isopropanol for 20 minutes. The substrates were dried under nitrogen flow, followed by treatment in a UV-Ozone chamber operating at 300 W for 20 minutes.

The cleaned substrates were then coated with an HIL ink formulation and dried at 90-170° C. for 5-15 minutes to form an HIL film layer. Dry film thicknesses ranged from approximately 20 nm to 60 nm. The coating process was done on a spin coater, but can be similarly achieved with spray coating, ink-jetting, contact printing, or any other deposition method capable of resulting in an HIL film of the desired thickness. The substrates were then transferred to a vacuum chamber where the remaining layers of the device stack were deposited by physical vapor deposition.

The devices thus obtained were encapsulated with a glass cover slip to prevent exposure to ambient conditions by means of a UV-light curing epoxy resin cured at 80 W/cm$^2$ UV exposure for 4 minutes.

Performance tests were conducted on the OLED devices of Example 6 and 7. Typically, performance is quantified by a combination of different parameters such as operating voltage (should be low), brightness in nits (should be bright, luminous), efficiency in units of cd/A (reflecting how much electric charge is needed to obtain light from the device), and the lifetime under operation (time required to reach half of the initial luminance value at the start of the test). As such, the overall performance is very important in a comparative evaluation of HIL performance. Performance of the devices was tested using the using the following procedures.

The OLED devices comprise pixels on a glass substrate whose electrodes extend outside the encapsulated area of the device which contain the light emitting portion of the pixels. The typical area of each pixel in such devices is 0.05 cm$^2$. To test the devices, the electrodes were contacted with a current source meter such as a Keithley 2400 source meter with a bias applied to the indium tin oxide electrode while the aluminum electrode is earthed. This procedure results in positively charged carriers (holes) and negatively charged carriers being injected into the device which form excitons and generate light. In the OLED devices of this example, the HIL layer of the device assists the injection of charge carriers into the light emitting layer, resulting in a low operating voltage of the device (defined as the voltage required to run a given current density through the pixel).

Simultaneously, another Keithley 2400 source meter was used to address a large area silicon photodiode. This photodiode was maintained at zero volts bias by the 2400 source meter and placed in direct contact with area of the glass substrate directly below the lighted area of the OLED pixel. The photodiode was used to collect the light generated by the OLED device, converting it into photocurrent which is in turn read by the source meter. The photodiode current generated is quantified into optical units (candelas/sq. meter) by calibrating it with the help of a Minolta CS-200 Chromameter.

Voltage-current-light or IVL data for the OLED pixels of the devices were generated as follows: During the testing of the device, the Keithley 2400 source meter addressing the OLED pixel applied a voltage sweep to it. The resultant current passing through the pixel was measured. At the same time, the current passing through the OLED pixel resulted in light being generated, which then resulted in a photocurrent reading by the other Keithley 2400 source meter connected to the photodiode. This in turn enabled the measurement of other device characteristics, such as the lumens per Watt of electrical input power to the pixel (power efficiency) and candelas per ampere of pixel current.

Current density (mA/cm$^2$), operating voltage (V), brightness (cd/m$^2$), and efficiency (cd/A) were measured for the OLED devices in Examples 6 and 7. These devices contained HILs formed from ink compositions 1-9 shown in Tables 1 and 2, and a comparative HIL per Table 3. The results are presented in Tables 4, 5, 6 and 7. In Tables 4-7, HILs 1-9 correspond to ink compositions 1-9 of Tables 1 and 2. The Comparative HIL was made as described above in Table 3. Nearly all devices containing a HIL formed from ink compositions 1-9 produced greater brightness and higher efficiency than those containing the comparative HIL.

Example 6

OLED Device Fabrication and Testing with poly(TPD-TFVBPA)

An ink composition comprising poly(TPD-TFVBPA) was cast as the hole injection layer of a device.

The device layers deposited on top of the HIL included a hole transporting layer (HTL), an emissive layer (EML), a hole blocking layer (HBL), an electron transporting layer (ETL), and a metal cathode. The materials used were N,N' (dinaphthalen-1-yl)-N,N'-diphenyl-benzidine (NPB) as the HTL, bis(2-methyl-8-quinolinolato-N1,O8)-(1,1'-biphenyl-4-olato)aluminum (BAlq) doped with tris-(1-phenylisoquinoline)iridium III (Ir(piq)3) for the EML, BAlq as the HBL, and tris(8-hydroxyquinoline)aluminium (Alq3) as the ETL. All of these materials are commercially available. The cathode layer was prepared by the sequential deposition of two metal layers, the first being a 3 nm to 5 nm layer of Ca (0.1 nm/sec) followed by a 200 nm layer of Al (0.5 nm/sec) with the base pressure at $5 \times 10^{-7}$ Torr.

FIG. 3 shows IVL measurements for devices 1, 2, 3 along with a Comparative HIL example.

The device performance of HILs 1-3 and Comparative HIL are summarized in Table 4. As can be seen, each of these non-aqueous HILs exhibit IVL performance that is comparable, if not better, than comparative aqueous HIL.

TABLE 4

Comparison of Inventive HILs 1-3 with the comparative HIL. Device Structure: ITO/HIL/NPB/BAlq:Ir(piq)3 (15 wt %)/BAlq/Alq3/Ca/Al

| HIL System | Device structure | Current Density (mA/cm$^2$) | Voltage (V) | Brightness (cd/m$^2$) | Efficiency (cd/A) |
|---|---|---|---|---|---|
| Comp HIL 1 For HIL (1-3) | ITO/HIL/NPB/BAlq:Ir(piq)3 (15 wt %)/BAlq/Alq3/Ca/Al | 27 | 12 | 1078 | 3.59 |
| HIL 1 | | 27 | 12.7 | 983 | 3.28 |
| HIL 2 | | 27 | 12.3 | 1130 | 3.78 |
| HIL 3 | | 27 | 12.9 | 1199 | 4.00 |

Example 7

OLED Device Fabrication and Testing with TPD-TFV (Example 2)

An ink composition comprising TPD-TFV was cast as the hole injection layer of a device. The layers deposited on top of the HIL included a hole transporting layer (HTL), an emissive layer (EML), a hole blocking layer (HBL), an electron transporting layer (ETL), and a metal cathode. The materials used were N,N'(dinaphthalen-1-yl)-N,N'-diphenyl-benzidine (NPB) as the HTL, bis(2-methyl-8-quinolinolato-N1,O8)-(1, 1'-biphenyl-4-olato)aluminum (BAlq) doped with tris-(1-phenylisoquinoline)iridium III (Ir(piq)$_3$) for the EML, Bis(2-methylquinolin-8-olato-κ$^2$N,O)(6-phenyl-2-naphtholato-κO)aluminium(III) (BAlq') and an electron transport layer ETL and an electron injection layer EIL. All of these materials are commercially available. The cathode layer was prepared by the sequential deposition of a 200 nm layer of Al (0.5 nm/sec) with the base pressure at $5 \times 10^{-7}$ Torr.

FIG. 10 $a,b$ show IVL measurement for devices 4, 5, 6 and comparative example. FIG. 11 $a, b$ show IVL measurement for devices 7, 8, 9 and comparative example.

TABLE 5

Comparison of HILs 4-9 with the comparative HIL. device Structure:
ITO/HIL/NPB/BAlq:Ir(piq)3 (15 wt %)/BAlq'/ETL/EIL/Al.

| HIL System | Device structure | Current Density (mA/cm2) | Voltage (V) | Brightness (cd/m2) | Efficiency (cd/A) |
|---|---|---|---|---|---|
| Comp HIL 1 For HIL (5-6) | ITO/HIL/NPB/BAlq:Ir(piq)3 (15 wt %)/BAlq'/ETL/EIL/Al | 27 | 10.1 | 981 | 3.27 |
| Inv HIL 5 | | 27 | 8.0 | 1094 | 3.65 |
| Inv HIL 6 | | 27 | 8.1 | 1035 | 3.45 |
| Comp HIL 1 For HIL (7-9) | | 27 | 7.59 | 974 | 3.25 |
| Inv HIL 7 | | 27 | 6.60 | 1255 | 4.18 |
| Inv HIL 8 | | 27 | 6.82 | 1220 | 4.07 |
| Inv HIL 9 | | 27 | 6.40 | 1174 | 3.91 |

In addition, OLED devices can also be tested for their lifetime performance. Lifetime performance can be measured using lifetime testers where a constant current is sourced through the tested devices. The current to the device is adjusted so that it gives a certain initial luminance value. For lifetime performance tests, this value is typically set at 1,000 candela/meter$^2$. The luminance decay and voltage rise over time are then noted.

OLED devices fabricated in a manner similar to those of Examples 5-7 above were tested for lifetime performance. The OLED devices contained the Comparative HIL and Inventive HIL used for the device efficiency measurements shown in Table 6, and had the general structure ITO/HIL/NPB/BAlq:Ir(piq)3 (15 wt %)/ETL/EIL/Al. The results of the lifetime performance tests are shown in Table 6. In general, devices containing the inventive HIL produced greater brightness and longer lifetimes than those containing the comparative HIL.

TABLE 6

Life test of Comparative and Inventive HILs. Device structure:
ITO/HIL/NPB/BAlq: Ir(piq)3 (15 wt %)/ETL/EIL/Al.

| HIL System | Device structure | Brightness (cd/m$^2$) under lifetest | Lifetime hrs (time to 50% of beginning luminance) |
|---|---|---|---|
| Comp HIL 1 For HIL (5-6) | ITO/HIL/NPB/ BAlq: | 2018 | 57 |
| Inv HIL 5 | Ir(piq)3 | 2020 | >900 |
| Inv HIL 6 | (15 wt %)/ | 2017 | >900 |
| Comp HIL 1 For HIL (7-9) | ETL/EIL/Al | 1996 | 28 |
| Inv HIL 7 | | 2020 | 1,128 |
| Inv HIL 8 | | 2086 | 403 |
| Inv HIL 9 | | 2083 | 1,600 |

Wash Studies

Example 8

Film Thickness of TPD-TFV Monomer with and without 1,1,1-Tris(4-trifluorovinyloxyphenyl)ethane (TFVOE)

Samples of TPD-TFV were synthesized according to the reaction scheme described above in Example 2. A sample comprising 5 wt % TPD-TFV dissolved in 95 wt % DOWANOL™ PMA propylene glycol methyl ether acetate (available from The Dow Chemical Company, Midland, Mich. 48674) was prepared as a reference solution. Several experimental solutions were prepared comprising 4.25-4.75 wt % TPD-TFV, 0.25-0.75 wt % TFVOE (Cat#019500 available from Oakwood Chemical, West Columbia, S.C. 29172), and 95 wt % DOWANOL™ PMA. A study was performed to measure the effects of addition of 0.25-0.75 wt % tri-functional component TFVOE to the TPD-TFV solution to the resulting films formed by such compositions. Specifically, solutions were spun onto ITO plates at 1000 rpm in a glove box, then annealed. A first thickness measurement ("Pre-Toluene") was obtained after the first anneal. The resulting films were then exposed to a toluene wash, spun at 4330 rpm, and annealed for an additional 15 minutes at 130° C. A second thickness measurement ("Post-Toluene") was then obtained. Film thickness measurements were obtained by ellipsometric technique. The results are shown in Table 7 below.

TABLE 7

Film Thickness Measurement Study.

| TPD-TFV (wt %) | TFVOE (wt %) | Solvent/solvent (wt %) | Anneal T ° C. | t min | Thickness, nm Pre-Toluene | Post-Toluene |
|---|---|---|---|---|---|---|
| 5 | 0 | Dowanol PMA/95% | 250 | 120 | 89 | 68 |
| 5 | 0 | Dowanol PMA/95% | 250 | 120 | 61 | 48 |
| 5 | 0 | Dowanol PMA/95% | 250 | 120 | 65 | 52 |
| 5 | 0 | Dowanol PMA/95% | 250 | 120 | 60 | 50 |
| 5 | 0 | Dowanol PMA/95% | 250 | 120 | 45 | 38 |
| 5 | 0 | Dowanol PMA/95% | 250 | 120 | 106 | 80 |
| 5 | 0 | Dowanol PMA/95% | 250 | 120 | 100 | 72 |
| 5 | 0 | Dowanol PMA/95% | 250 | 120 | 93 | 71 |

TABLE 7-continued

Film Thickness Measurement Study.

| TPD-TFV (wt %) | TFVOE (wt %) | Solvent/solvent (wt %) | Anneal T ° C. | Anneal t min | Thickness, nm Pre-Toluene | Thickness, nm Post-Toluene |
|---|---|---|---|---|---|---|
| 4.75 | 0.25 | Dowanol PMA/95% | 250 | 120 | 73 | 67 |
| 4.75 | 0.25 | Dowanol PMA/95% | 250 | 120 | 59 | 53 |
| 4.25 | 0.75 | Dowanol PMA/95% | 250 | 120 | 45 | 48 |
| 4.25 | 0.75 | Dowanol PMA/95% | 250 | 120 | 49 | 52 |
| 4.75 | 0.25 | Dowanol PMA/95% | 250 | 120 | 63 | 57 |
| 4.75 | 0.25 | Dowanol PMA/95% | 250 | 120 | 58 | 55 |
| 4.25 | 0.75 | Dowanol PMA/95% | 250 | 120 | 51 | 53 |
| 4.25 | 0.75 | Dowanol PMA/95% | 250 | 120 | 53 | 55 |

The data in Table 7 show that for films without the TFVOE, a toluene wash between annealing results in some loss in film thickness. Where TFVOE is present in the solution and resulting film, a similar toluene wash causes little, if any, change in thickness. An increase of TFVOE from 0.25 wt % to 0.75 wt % TFVOE in prepared solutions results in decreased losses in thickness after toluene wash. These results provide a pathway for protecting underlying films that would otherwise be washed away upon depositing additional layers from inks comprising organic solvents.

Example 9

Synthesis and Study of N3,N6-diphenyl-N3,N6,9-tris(4-(1,2,2-trifluorovinyloxy)phenyl)-9H-carbazole-3,6-diamine (Cz-TFV)

1. Synthesis

Synthesis of N3,N6-diphenyl-N3,N6,9-tris(4-(1,2,2-trifluorovinyloxy)phenyl)-9H-carbazole-3,6-diamine (compound 4 below) was carried out according to the following reaction scheme.

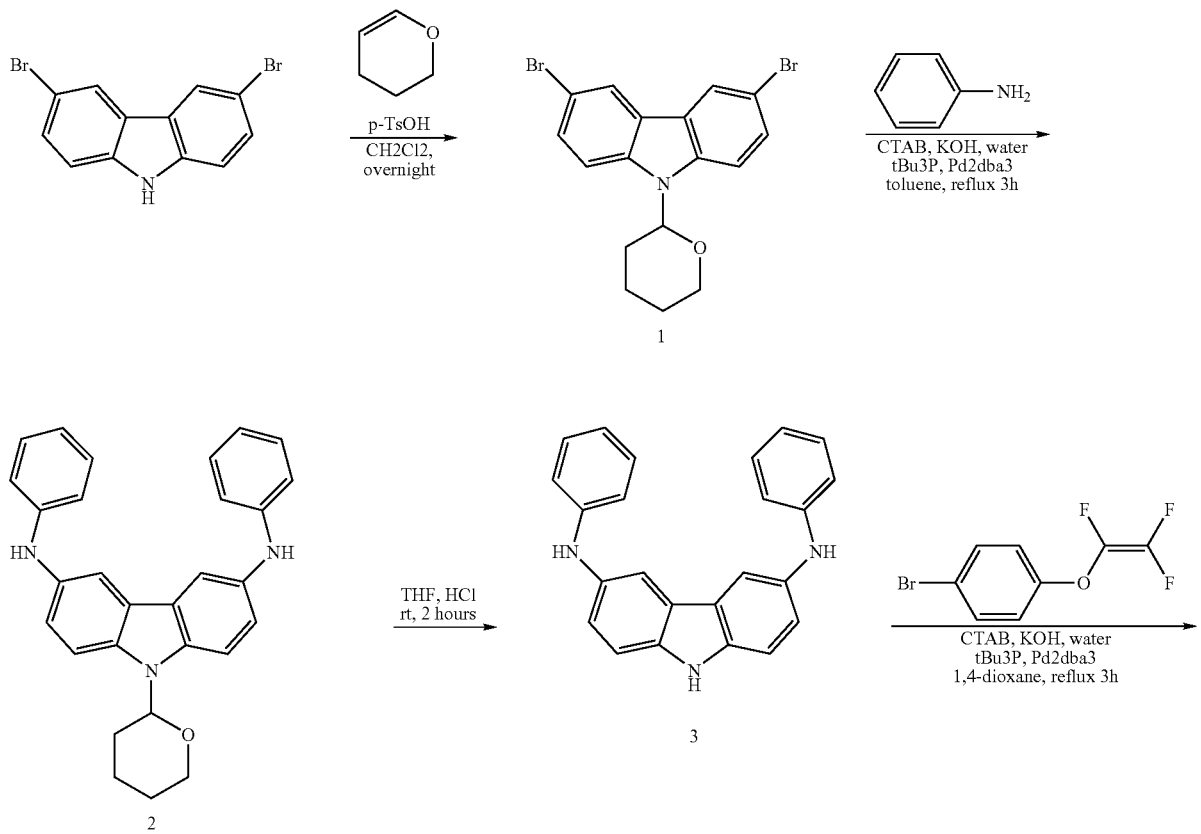

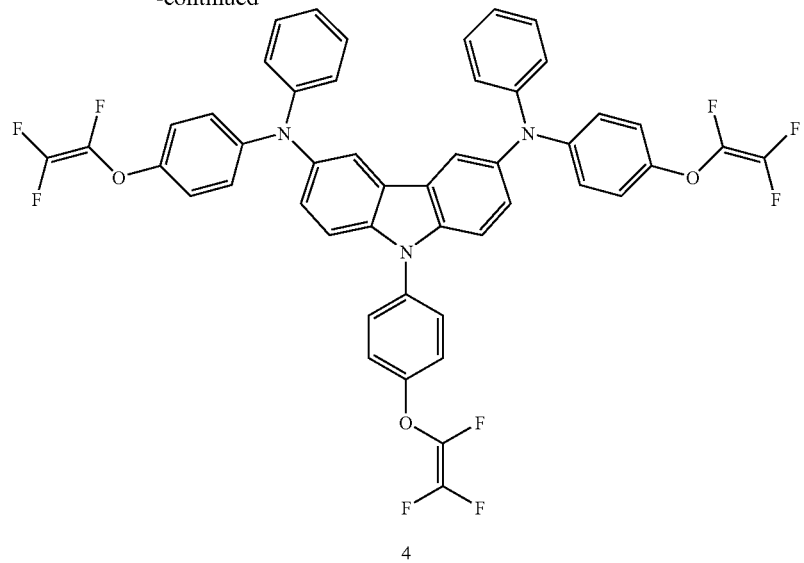

A first reaction produces compound (1) according to the scheme below:

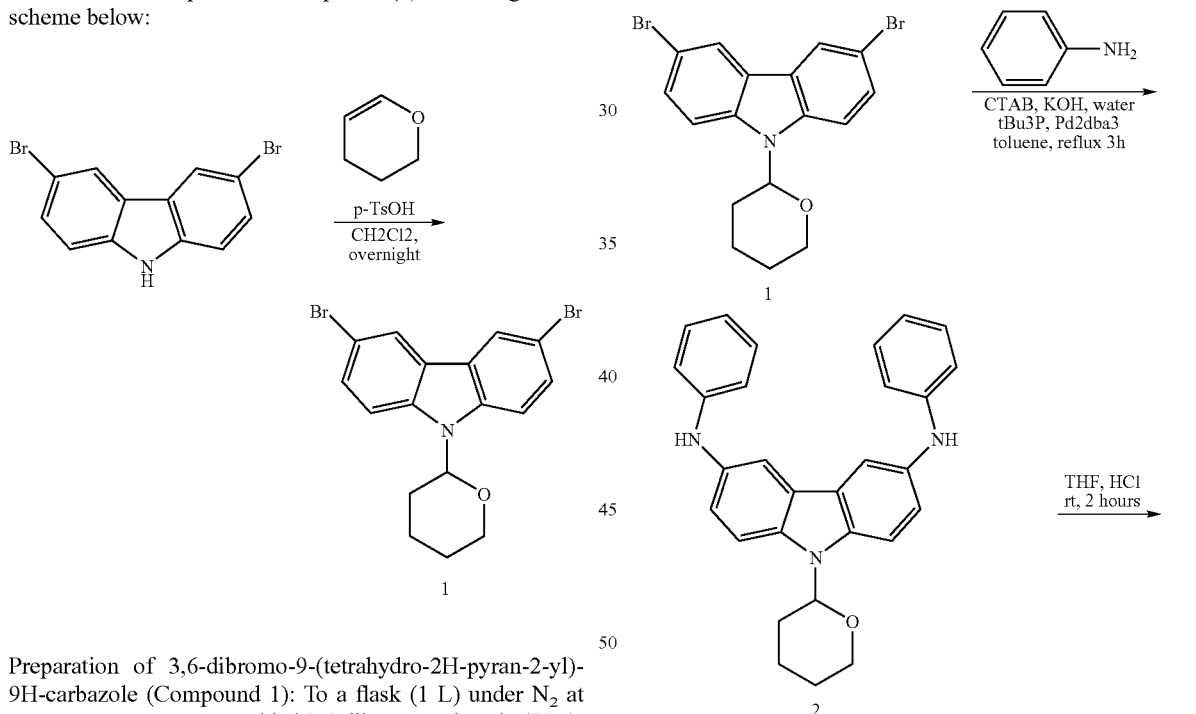

Preparation of 3,6-dibromo-9-(tetrahydro-2H-pyran-2-yl)-9H-carbazole (Compound 1): To a flask (1 L) under $N_2$ at room temperature, were added 3,6-dibromocarbazole (50 g), dichloromethane (500 mL), 3,4-dihydro-2H-pyran (40 g), p-toluenesulfonic acid monohydrate (1 g). The reaction was stirred overnight. $NaHCO_3$ (3 g) was added, and the reaction was stirred for 1 h. After filtration, the solvent in the filtrate was removed by evaporation. MeOH (1 L) was added for reflux under $N_2$ for 2 h. Filtration when it was warm gave 37.5 g product. The MeOH (800 mL) was removed by evaporation, and solid came out. Filtration gave 12.5 g product. Both products are white, single spot on TLC, and GS-MS and $^1$H NMR showed they are pure product. The overall yield is 80%.

Second and Third Reactions following the reaction scheme above produce compound (2) and (3), respectively, according to the scheme below:

Preparation of N3,N6-diphenyl-9H-carbazole-3,6-diamine (Compound 3): To a dried flask under $N_2$, were added 3,6-dibromo-9-(tetrahydro-2H-pyran-2-yl)-9H-carbazole (1) (37.5 g), aniline (25 mL), hexadecyltrimethylammonium bromide (430 mg), aqueous potassium hydroxide (68.6 g, 45% in water), toluene (1.2 L). The stirred mixture was purged with $N_2$ for 15 min. Then to this mixture, were added $Pd_2$ $dba_3$ (4.12 g) and tri-tert-butylphosphine (2.97 g in anhydrous toluene). The reaction was heated to reflux overnight. The reaction was cooled down to room temperature, and anhydrous $MgSO_4$ was added, and filtered through a layer of silica gel and celite. The solvent was removed and crude product was used for next reaction without purification. To a 2 L flask under $N_2$, was added all the crude product of N3,N6-diphenyl-9-(tetrahydro-2H-pyran-2-yl)-9H-carbazole-3,6-diamine (2), THF (1 L), and concentrated HCl (20 mL). The reaction mixture was stirred for 2 h. The THF (700 mL) was removed by evaporation, and then poured into ice water, filtered to obtain the solid crude product. The solid was stirring in ethyl acetate (500 mL) for 2 h, and filtration gave the final product (13.7 g) in 42% yield for two steps. $^1$H NMR was consistent with the compound.

A fourth reaction to prepare compound 4 follows is carried out as follows:

Preparation of N3,N6-diphenyl-N3,N6,9-tris(4-(1,2,2-trifluorovinyloxy)phenyl)-9H-carbazole-3,6-diamine (Cz-TFV; Compound 4): To a dried flask under $N_2$, were added N3,N6-diphenyl-9H-carbazole-3,6-diamine (3) (5 g), 1-bromo-4-(trifluorovinyloxy)benzene (14.5 g), hexadecyltrimethylammonium bromide (313 mg), aqueous potassium hydroxide (17.8 g, 45% in water), 1,4-dioxane (500 mL). The stirred mixture was purged with $N_2$ for 15 min. Then to this mixture, were added Pd2 dba3 (1.2 g) and tri-tert-butylphosphine (0.75 g in anhydrous toluene). The reaction was heated to reflux overnight. The reaction was cooled down to room temperature, and was added anhydrous $MgSO_4$, and filtered through a layer of silica gel and celite. The solvent was removed and the crude product was purified using a silica plug (hexane, and then 1% EtOAc in hexane), and then was further purified using automatic column (hexane). 4.8 g pure product in 39% yield was obtained. $^1$H, $^{13}$C and $^{19}$F NMR were consistent with the compound.

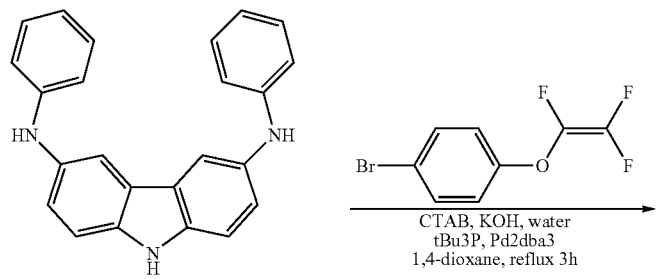

3

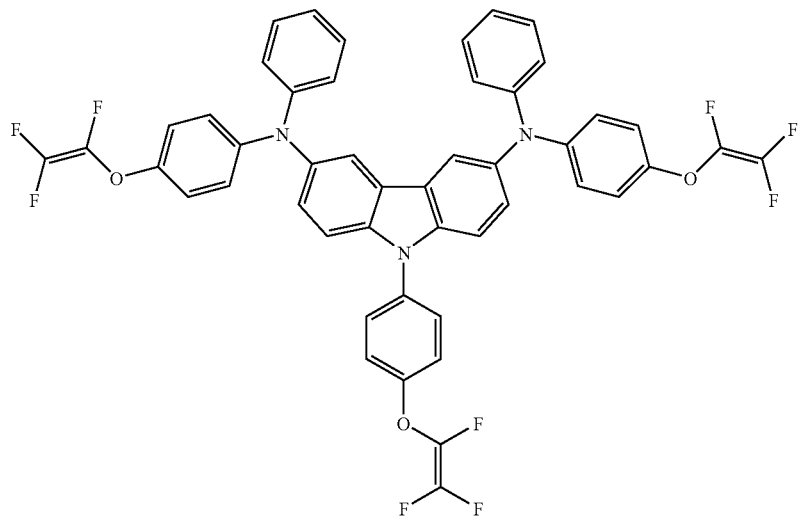

4

2. Formulations:

| HTL | Material | TS | Solvent |
|---|---|---|---|
| 1 | 100% TPD-TFV | 2% | PMA |
| 2 | 95% TPD-TFV + 5% TFVOE | 5% | PMA |
| 3 | 100% Cz-TFV | 5% | Toluene |
| 4 | 100% Cz-TFV | 3% | Toluene |

TS = total solids

3. Properties of Cz-TFV

The film was from the spinning conditions of 1,000 rpm/60 s in glove box and annealing conditions were 250° C./60 min in glove box on glass.

UV-vis: $\lambda_{max}$=311 nm, PL: $\lambda_{max}$=425 nm

Figure 12:
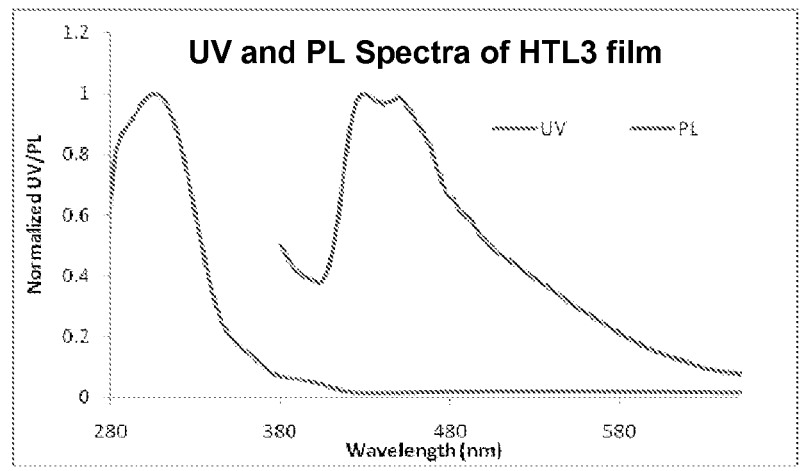
FIG. 12 shows UV and photoluminescent spectra of HTL 3 film.

See FIG. 12

Transparency: >95% when $\lambda$=462 nm

Figure 13:
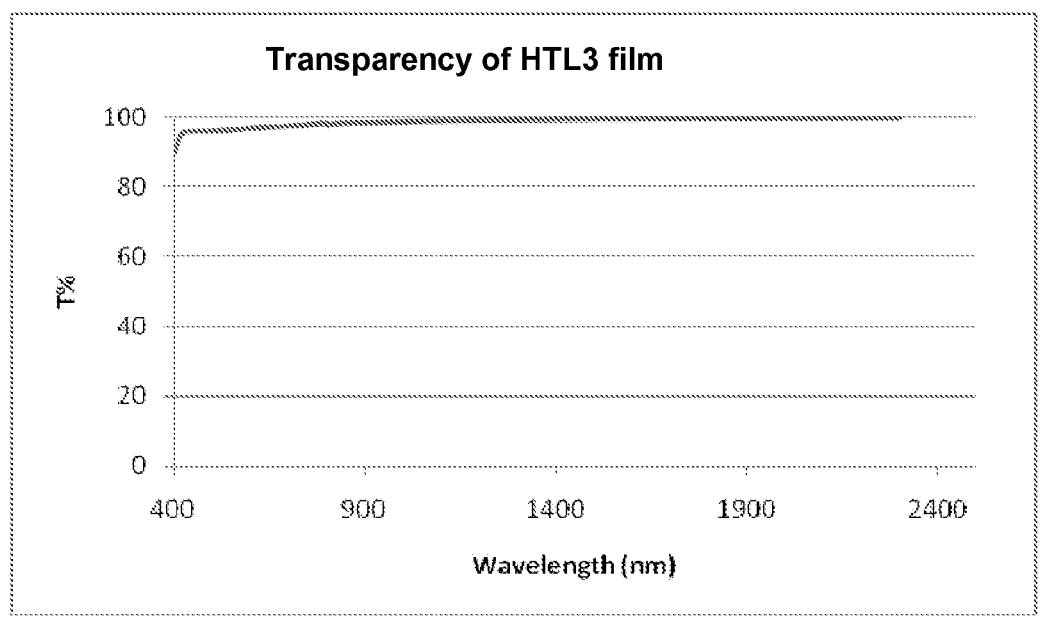
FIG. 13 shows transparency measurement of HTL 3 film.

See FIG. 13.

Further Film Study

Propylene Glycol Methyl Ether Acetate (PMA)

Spinning conditions: 1000 rpm/60 s in glove box

Annealing conditions: 250° C./60 min in glove box

Good film means smooth, clear, and uniform films by visional observation.

ITO Substrate

Cross-Linking Reaction in Films

Cross-linking reaction in films was monitored by FTIR. 1833 cm$^{-1}$ peak is weak, and 965 cm$^{-1}$ peak was used to monitor the cross-linking reaction in films Annealing temperature 150, 200, and 250 C, and annealing time 2, 15, 60 min at these temperatures are studied for HTL 1. There is no peak increase at 250 C/60 min. However, the film does not remain after toluene wash. Therefore, 5% TFVOE was added to the formulation HTL2.

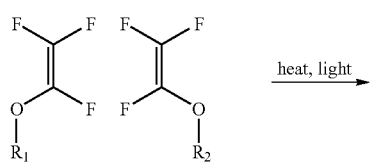

CF=CF2 peak at 1833 cm$^{-1}$.
Very weak, hard to follow.

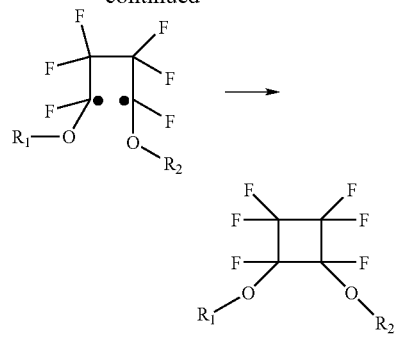

PFCB ring peaks appear at 965 cm$^{-1}$.
Strong to follow

Film Formation and Wash Study on ITO

HTL2, HTL3 and HTL4 are able to form good films on ITO, and have 90-100% film retain after toluene/chlorobenzene wash. Cz-TFV has three cross-linking groups, and performs better for film retain than TPD-TFV.

| Film # | HTL | Pre wash Film Quality | Thickness nm | Wash Solvent | Post Wash Film Quality | Thickness nm | Film Retain % |
|---|---|---|---|---|---|---|---|
| 1 | HTL2 | Good | 73 | Toluene | Good | 67 | 92 |
| 2 | HTL2 | Good | 59 | Toluene | Good | 53 | 89 |
| 3 | HTL2 | Good | 63 | Chlorobenzene | Good | 57 | 91 |
| 4 | HTL2 | Good | 58 | Chlorobenzene | Good | 55 | 95 |
| 5 | HTL3 | Good | 111 | Toluene | Good | 114 | 103 |
| 6 | HTL3 | Good | 112 | Toluene | Good | 114 | 102 |
| 7 | HTL4 | Good | 66 | Toluene | Good | 67 | 102 |
| 8 | HTL4 | Good | 66 | Toluene | Good | 69 | 106 |
| 9 | HTL3 | Good | 109 | Chlorobenzene | Good | 111 | 102 |
| 10 | HTL3 | Good | 113 | Chlorobenzene | Good | 114 | 101 |

(1) Film Formation on HIL Comp2, and Non-aq HILs Comp3 and 4

HTL 3 is able to form good films on both aq-HIL and non-aq HILs with consistent thickness.

| Film # | HIL | HTL | Overall Average | Thickness of Single Layer | |
|---|---|---|---|---|---|
| 1 | Comp2 | No | 66 | Comp2 | 66 |
| 2 | Comp2 | HTL3 | 173 | HTL3 | 107 |
| 3 | Comp3 | No | 21 | Comp3 | 21 |
| 4 | Comp3 | HTL3 | 137 | HTL3 | 116 |
| 5 | Comp4 | No | 31 | Comp4 | 31 |
| 6 | Comp4 | HTL3 | 135 | HTL3 | 104 |

(4) UV and Thermal Annealing

The UV and thermal annealing all have 90-100% film thickness retained after toluene wash. But the UV annealing gave thicker films. Substrate is ITO.

| HTL | Pre-annealing | Annealing | Pre-toluene wash | Post-toluene wash | film remain % |
|---|---|---|---|---|---|
| HTL2 | 150 C/15 min to remove | No | 56 | 13 | 24 |
| | | No | 57 | 18 | 31 |

-continued

| HTL | Pre-annealing | Annealing | Pre-toluene wash | Post-toluene wash | film remain % |
|---|---|---|---|---|---|
| | solvent | 250 C/60 min | 26 | 27 | 101 |
| | | 250 C/60 min | 28 | 27 | 95 |
| | | UV/30 min | 49 | 44 | 89 |
| | | UV/30 min | 47 | 43 | 92 |

What is claimed is:

1. A device comprising a layer comprising an oligomer or polymer comprising repeat units represented by $$-\!(\!O\!-\!Ar^1\!)\!-\text{and} \tag{I}$$

$$-\!(\!O\!-\!R^1\!-\!O\!-\!Ar^2\!-\!O\!-\!R^2\!)\!- \tag{II}$$

wherein, $Ar^1$ is an arylamine, $Ar^2$ comprises an aryl, and $R^1$ and $R^2$ are independently selected from $C_1$-$C_{10}$ fluorinated alkylene, wherein said layer is a hole injection layer.

2. The device of claim 1, wherein said device is an organic light-emitting diode, polymer light emitting diode, phosphorescent organic light-emitting diode or organic photovoltaic device.

3. The device of claim 1, wherein said oligomer or polymer is doped.

4. The device of claim 1, wherein the repeat units (I) and (II) are alternating.

5. The device of claim 1, wherein $Ar^1$ is represented by

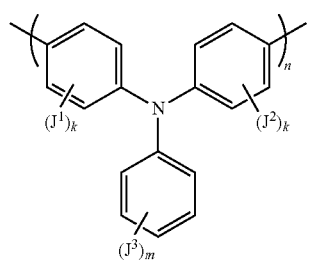

(III)

wherein, $J^1$, $J^2$ and $J^3$ are independently selected from hydrogen, $C_1$-$C_{10}$ alkyl, perfluoroalkyl, thioalkyl, alkoxy, alkylaryl, arylalkyl, aryloxy, heteroaryl, cyano, halo and alkylthio groups, k is an integer from 1 to 4, m is an integer from 1 to 5, and n is an integer from 1 to 5;

or wherein $Ar^1$ is represented by

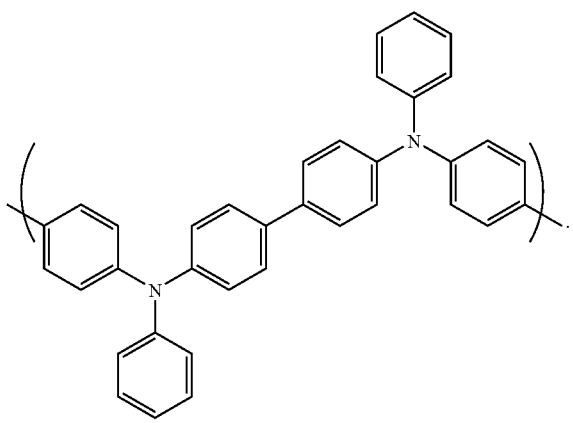

(IV)

6. The device of claim 1, wherein $Ar^2$ is represented by

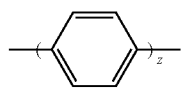

(V)

wherein z is an integer from 1 to 5;

or wherein $Ar^2$ is represented by:

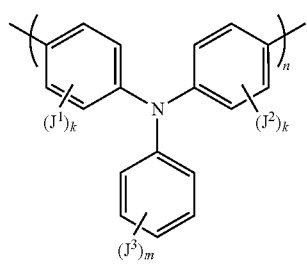

(III)

wherein, $J^1$, $J^2$ and $J^3$ are independently selected from hydrogen, $C_1$-$C_{10}$ alkyl, perfluoroalkyl, thioalkyl, alkoxy, alkylaryl, arylalkyl, aryloxy, heteroaryl, cyano, halo and alkylthio groups, k is an integer from 1 to 4, m is an integer from 1 to 5, and n is an integer from 1 to 5;

or wherein $Ar^2$ is represented by

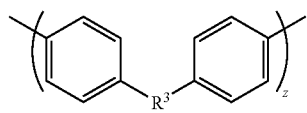

(VI)

wherein, $R^3$ is an optionally fluorinated $C_1$-$C_{10}$ alkyl, and

Z is an integer from 1 to 5;

or wherein Ar² is represented by

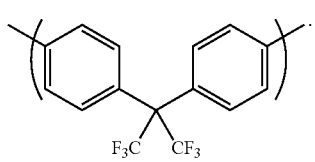
(VII)

7. The device of claim 1, wherein the oligomer or polymer is insoluble and crosslinked.

8. The device of claim 1, wherein the oligomer or polymer is soluble.

9. A device comprising a layer comprising an oligomer or polymer comprising repeat units represented by $$-(O-Ar^1)- \text{ and} \quad (I)$$

$$-(O-R^1-O-Ar^2-O-R^2)- \quad (II)$$

wherein,

Ar¹ is an arylamine,

Ar² comprises an aryl, and

R¹ and R² are independently selected from $C_1$-$C_{10}$ fluorinated alkylene, wherein said layer is an electron blocking layer.

10. The device of claim 9, wherein said device is an organic light-emitting diode, polymer light emitting diode, phosphorescent organic light-emitting diode or organic photovoltaic device.

11. The device of claim 9, wherein said oligomer or polymer is doped.

12. The device of claim 9, wherein the repeat units (I) and (II) are alternating.

13. The device of claim 9, wherein Ar¹ is represented by

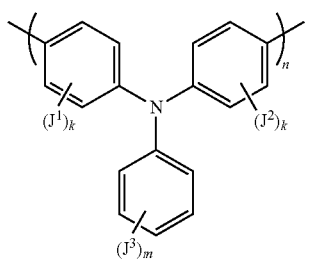
(III)

wherein,

J¹, J² and J³ are independently selected from hydrogen, $C_1$-$C_{10}$ alkyl, perfluoroalkyl, thioalkyl, alkoxy, alkylaryl, arylalkyl, aryloxy, heteroaryl, cyano, halo and alkylthio groups, k is an integer from 1 to 4, m is an integer from 1 to 5, and n is an integer from 1 to 5;

or wherein Ar¹ is represented by

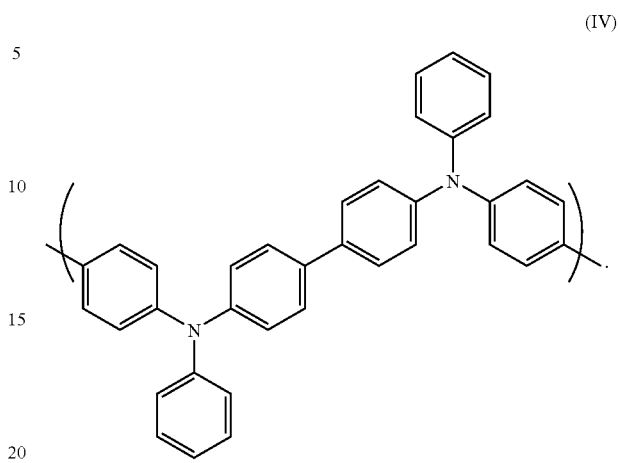
(IV)

14. The device of claim 9, wherein Ar² is represented by $$\text{(V)}$$

wherein z is an integer from 1 to 5;
or wherein Ar² is represented by:

(III)

wherein,

J¹, J² and J³ are independently selected from hydrogen, $C_1$-$C_{10}$ alkyl, perfluoroalkyl, thioalkyl, alkoxy, alkylaryl, arylalkyl, aryloxy, heteroaryl, cyano, halo and alkylthio groups, k is an integer from 1 to 4, m is an integer from 1 to 5, and n is an integer from 1 to 5;

or wherein Ar² is represented by

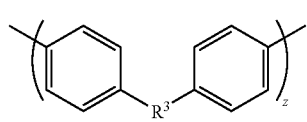
(VI)

wherein,

R³ is an optionally fluorinated $C_1$-$C_{10}$ alkyl, and

Z is an integer from 1 to 5;

or wherein Ar² is represented by

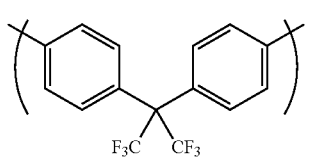
(VII)

15. The device of claim 9, wherein the oligomer or polymer is insoluble and crosslinked.

16. The device of claim 9, wherein the oligomer or polymer is soluble.

17. A device comprising a layer comprising an oligomer or polymer comprising repeat units represented by –(O—Ar¹)– and   (I)

–(O—R¹—O—Ar²—O—R²)–   (II)

wherein,

Ar¹ is an arylamine,

Ar² comprises an aryl, and

R¹ and R² are independently selected from $C_1$-$C_{10}$ fluorinated alkylene, wherein said oligomer or polymer is doped.

18. The device of claim 17, wherein said device is an organic light-emitting diode, polymer light emitting diode, phosphorescent organic light-emitting diode or organic photovoltaic device.

19. The device of claim 17, wherein said layer is a hole transport layer.

20. The device of claim 17, wherein the repeat units (I) and (II) are alternating.

21. The device of claim 17, wherein Ar¹ is represented by

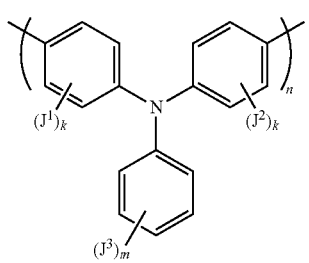
(III)

wherein,

J¹, J² and J³ are independently selected from hydrogen, $C_1$-$C_{10}$ alkyl, perfluoroalkyl, thioalkyl, alkoxy, alkylaryl, arylalkyl, aryloxy, heteroaryl, cyano, halo and alkylthio groups, k is an integer from 1 to 4, m is an integer from 1 to 5, and n is an integer from 1 to 5;

or wherein Ar¹ is represented by

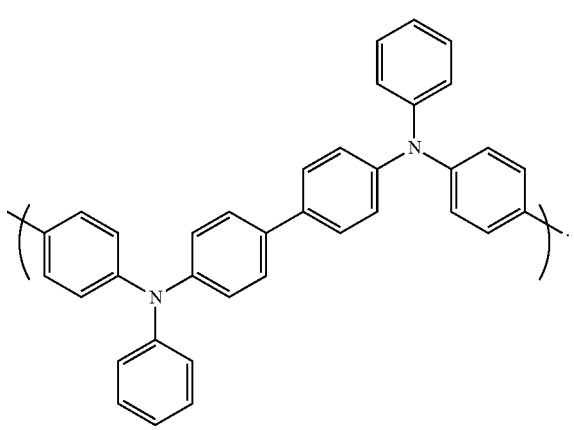
(IV)

22. The device of claim 17, wherein Ar² is represented by (V)

wherein z is an integer from 1 to 5;

or wherein Ar² is represented by:

(III)

wherein,

J¹, J² and J³ are independently selected from hydrogen, $C_1$-$C_{10}$ alkyl, perfluoroalkyl, thioalkyl, alkoxy, alkylaryl, arylalkyl, aryloxy, heteroaryl, cyano, halo and alkylthio groups, k is an integer from 1 to 4, m is an integer from 1 to 5, and n is an integer from 1 to 5;

or wherein Ar² is represented by

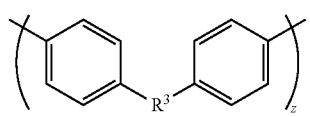
(VI)

wherein,

R³ is an optionally fluorinated $C_1$-$C_{10}$ alkyl, and

Z is an integer from 1 to 5;

or wherein Ar² is represented by
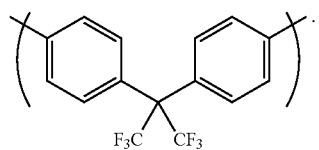
(VII)
23. The device of claim 17, wherein the oligomer or polymer is insoluble and crosslinked.
24. The device of claim 17, wherein the oligomer or polymer is soluble.
* * * * *